United States Patent
He et al.

(10) Patent No.: US 9,538,745 B2
(45) Date of Patent: Jan. 10, 2017

(54) METHODS FOR THE CRYOPRESERVATION OF CELLS

(75) Inventors: Xiaoming He, Winchester, MA (US);
Thomas L. Toth, Sudbury, MA (US);
Mehmet Toner, Wellesley, MA (US);
Jon Edd, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 822 days.

(21) Appl. No.: 12/226,300

(22) PCT Filed: Apr. 12, 2007

(86) PCT No.: PCT/US2007/009142
§ 371 (c)(1),
(2), (4) Date: Jun. 18, 2009

(87) PCT Pub. No.: WO2007/120829
PCT Pub. Date: Oct. 25, 2007

(65) Prior Publication Data
US 2009/0305224 A1 Dec. 10, 2009

Related U.S. Application Data

(60) Provisional application No. 60/792,019, filed on Apr. 14, 2006, provisional application No. 60/792,020, filed on Apr. 14, 2006, provisional application No. 60/854,880, filed on Oct. 27, 2006.

(51) Int. Cl.
*A01N 1/02* (2006.01)

(52) U.S. Cl.
CPC .............. *A01N 1/02* (2013.01); *A01N 1/0221* (2013.01); *A01N 1/0268* (2013.01); *A01N 1/0278* (2013.01)

(58) Field of Classification Search
CPC ...... A01N 1/02; A01N 1/0278; A01N 1/0268; A01N 1/0221
See application file for complete search history.

(56) References Cited

U.S. PATENT DOCUMENTS

| | | | |
|---|---|---|---|
| 5,131,997 A | 7/1992 | Christianson et al. | |
| 5,833,827 A | 11/1998 | Anazawa et al. | |
| 5,900,132 A | 5/1999 | Keenan et al. | |
| 6,395,467 B1 | 5/2002 | Fahy et al. | |
| 6,402,918 B1 | 6/2002 | Schlenoff et al. | |
| 6,544,396 B1 | 4/2003 | Cong et al. | |
| 6,673,607 B2 * | 1/2004 | Toner et al. | 435/374 |
| 2001/0010747 A1 | 8/2001 | Dourdeville et al. | |
| 2002/0092770 A1 | 7/2002 | Hedberg et al. | |
| 2004/0206491 A1 * | 10/2004 | Davidson et al. | 165/185 |
| 2007/0267573 A1 | 11/2007 | Astorga-Wells | |
| 2010/0108513 A1 | 5/2010 | Amirkhanian | |

FOREIGN PATENT DOCUMENTS

JP 06323987 11/1994
WO WO 2007/120829 10/2007

OTHER PUBLICATIONS

Cremades et al. Experimental vitrification of human compacted morulae and early blastocysts using ® ne diameter plastic micropipettes. Human Reproduction vol. 19, No. 2 pp. 300±305, 2004.*
Temperature scales and Absolute zero. Downloaded on Feb. 7, 2012 from http://cryo.gsfc.nasa.gov/introduction/temp_scales.html. p. 1-2.*
PubChem compound summary for ethylene glycol. downloaded on Feb. 7, 2012 from http://pubchem.ncbi.nlm.nih.gov/summary/summary.cgi?cid=174&loc=ec_rcs. p. 1-2.*
PubChem compound summary for DMSO. downloaded on Feb. 7, 2012 from pubchem.ncbi.nlm.nih.gov/summary/summary.cgi?cid=679&loc=ec_rcs. p. 1-3.*
Asada et al. Effect of polyvinyl alcohol (PVA) concentration during vitrification of in vitro matured bovine oocytes. Theriogenology 58:1199-1208. 2002.*
Cho et al. Improvement in post-thaw viability of in vitro-produced bovine blastocysts vitrified by glass micropipette (GMP). Animal Reproduction Science 73 (2002) 151-158.*
Thermal conductivity. 2012. downloaded from http://hyperphysics.phy-astr.gsu.edu/hbase/tables/thrcn.html. p. 1-3.*
Heat Conduction. downloaded on Feb. 8, 2012 from web.archive.org/web/20011123135931/http://hyperphysics.phy-astr.gsu.edu/hbase/thermo/heatcond.html. p. 1.*
Charles Supper Company webpage. downloaded on Feb. 8, 2012 from web.archive.org/web/19980416163627/http://charles-supper.com/price2.htm. p. 1-2.*
Wilson et al. Ice nucleation in nature: supercooling point (SCP) measurements and the role of heterogeneous nucleation. Cryobiology 46 (2003) 88-98.*
Isachenko et al.Cryopreservation of human ovarian tissue by direct plunging into liquid nitrogen. European Journal of Obstetrics & Gynecology and Reproductive Biology 108 (2003) 186-193.*
Kasai. Cryopreservation of animal and human embryos by vitrification. vol. 9. No. 2. 2004 164-170 Reproductive BioMedicine Online.*

(Continued)

*Primary Examiner* — Taeyoon Kim
(74) *Attorney, Agent, or Firm* — Fish & Richardson P.C.

(57) ABSTRACT

The present invention features novel methods for the cryopreservation of mammalian cell that combine the advantages of the slow-freezing and vitrification approaches while avoiding their shortcomings. Generally, the methods include the use of a capillary tube made of a thermally conductive wall material and a thin wall such that the ratio of the thermal conductivity of the wall material to the wall thickness is at least 1,000-500,000. The solution is then exposed to temperatures equal to or less than −80° C. and the vitrification solution containing the mammalian cells is cooled at a rate equal to or greater than 30,000-100,000,000° C./minute. The exposure of the capillary tube with a thermally conductive and thin wall allows for vitrification of the solution in the absence of ice formation. Cryoprotectants can also be added to the vitrification solution to further prevent ice formation.

35 Claims, 21 Drawing Sheets

(56) References Cited

OTHER PUBLICATIONS

Mazur et al. Contributions of Cooling and Warming Rate and Developmental Stage to the Survival of Drosophila Embryos Cooled to −205° C. Cryobiology. vol. 30, Issue 1, Feb. 1993, pp. 45-73 (abstract only).*
Liebermann. Recent developments in human oocyte, embryo and blastocyst vitrification: where are we now? vol. 7. No. 6. 623-633 Reproductive BioMedicine Online; www.rbmonline.com/Article/975 on web Jul. 23, 2003.*
Mukaida et al. Vitrification of human embryos based on the assessment of suitable conditions for 8-cell mouse embryos. Human Reproduction vol. 13 No. 1 0 pp. 2874-2879, 1998.*
Chen et al., "Open Pulled Straws for Vitrification of Mature Mouse Oocytes Preserve Patterns of Meiotic Spindles and Chromosomes Better Than Conventional Straws," Human Production 15:2598-2603, 2000.
Choi et al., "Anomalous Thermal Conductivity Enhancement in Nanotube Suspensions," Applied Physics Letter 79:2252-2254, 2001.
International Search Report; Application No. PCT/US07/09142; mailed Aug. 5, 2008, 2 pages.
Ushijima et al., "Improved Survival of Vitrified in vivo-derived Porcine Embryos," Journal of Reproduction and Development 50:481-486, 2004.
Fujioka et al., "A simple and efficient Cryopreservation method for primate embryonic stem cells," Int. J. Dev. Biol., 48:1149-1154 (2004).
Heng et al., "The cryopreservation of human embryonic stem cells," Biotechnol. Appl. Biochem., 41:97-104 (2005).
Isachenko et al., "Cryoprotectnat-Free Cryopreservation of Human Spermatozoa by Vitrification and Freezing in Vapor: Effect on Motility, DNA Integrity, and Fertilization Ability," Biology of Reproduction, 71:1167-1173 (2004).
Isachenko et al., "DNA integrity and motility of human spermatozoa after standard slow freezing versus cryoprotectant-free vitrification," Human Reproduction, 19(4):932-939 (2004).
Isachenko, Eugenia, "Vitrification of mammalian spermatozoa in the absence of cryoprotectants: from past practical difficulties to present success," Reproductive BioMedicine Online; www.rbmonline.com/Article/791 on web (Jan. 10, 2003).
Isachenko, Vladimir, "Clean technique for cryoprotectant-free vitrification of human spermatozoa," Reproductive BioMedicine Online, www.rbmonline.com/Article/1637 (Jan. 25, 2005).
Ji et al., "Cryopreservation of Adherent Human Embryonic Stem Cells," Biotechnology and Bioengineering, 88(3): 299-312 (2004).
Katkov et al., "Low- and high temperature vitrification as a new approach to biostabilization of reproductive and progenitor cells," Int. J. Refrig., 29:346-357 (2006).
Reubinoff et al., "Effective cryopreservation of human embryonic stem cells by the open pulled straw vitrification method," Human Reproduction, 16(10):217-2194 (2001).
Richards et al., "An Efficient and Safe Xeno-Free Cryopreservation Method for the Storage of Human Embryonic Stem Cells," Stem Cells, 22:779-789 (2004).
Nawroth et al., "Vitrification of Human Spermatozoa Without Cryoprotectants," CryoLetters, 23:93-102 (2002).
Non-Final Office Action issued in U.S. Appl. No. 14/879,742 on Mar. 1, 2016 (8 pages).
Criado et al., "Human oocyte ultravitrification with a low concentration of cryoprotectants by ultrafast cooling: a new protocol," Fertility and Sterility, 95(3):1101-1103 (2011).
Gook and Edgar, "Human oocyte cryopreservation," Human Reproduction Update 13(6):591-605 (2007).
He et al., "Vitrification by ultra-fast cooling at a low concentration of cryoprotectants in a quartz micro-capillary. A study using murine embryonic stem cells," Cryobiology 56(3):223-232 (2008).
International Preliminary Report on Patentability in International Application No. PCT/US07/09142, dated Oct. 14, 2008, 7 pages.
International Preliminary Report on Patentability in International Application No. PCT/US2010/053057, dated Apr. 17, 2012, 6 pages.
International Search Report and Written Opinion in International Application No. PCT/US2010/053057, dated Aug. 11, 2011, 10 pages.
Lee et al., "Ultra-rapid vitrification of mouse oocytes in low cryoprotectant concentrations," Reproductive BioMedicine Online (2009), doi:10.1016/j.rbmo.2009.11.012.
Risco et al., "Thermal performance of quartz capillaries for vitrification," Cryobiology 55:222-229 (2007).

\* cited by examiner

METHODS FOR THE CRYOPRESERVATION OF CELLS

CROSS REFERENCE TO RELATED APPLICATIONS

This application is the U.S. National Stage of International Application No. PCT/US2007/09142, filed Apr. 12, 2007, which claims benefit of U.S. Provisional Application No. 60/792,019, filed Apr 14, 2006, U.S. Provisional Application No. 60/792,020, filed Apr. 14, 2006, and U.S. Provisional Application No. 60/854,880, filed Oct. 27, 2006, each of which is hereby incorporated by reference.

STATEMENT OF FEDERALLY SPONSORED RESEARCH

This invention was made with U.S. Government support under Grant No. DK046270 awarded by the National Institutes of Health. The U.S. Government has certain rights in this invention.

BACKGROUND OF THE INVENTION

The invention relates to methods for the cryopreservation of mammalian cells.

Effective long-term storage of mammalian cells is critical to the successful application of such cells as clinical and research tools. Oocytes, embryos, and stem cells are a small subset of the types of cells that are useful in the clinical setting. For example, stem cells can be used in cell based therapeutics, cryopreserved oocytes, sperm, and embryos can be used in assisted reproductive technologies, and stem cells or additional cell types can be used for cell transplantation, tissue engineering, and regenerative medicine.

There are two traditional approaches to the cryopreservation of biological material, slow freezing and vitrification. During slow freezing the cells are cooled to temperatures slightly below their equilibrium freezing point and ice is seeded in the extracellular media. As ice forms in the extracellular solution, there is a progressive increase in the external solute concentration. As a result, the cell dehydrates, the melting point of the cytoplasm lowers and the formation of intracellular ice is avoided. However, there are some disadvantages to using this approach: cell injury is thought to be due to the effects of exposure to highly concentrated intracellular and extracellular solutions and/or mechanical interactions between the cells and ice. Other disadvantages to slow freezing are the result of limitations in practicality: slow freezing requires the cooling rate as well as the seeding temperature to be well controlled, an additional drawback that may be responsible for the highly variable results of this technique.

Vitrification is the solidification of a sample while maintaining the absence of both intracellular and extracellular ice. This glassy state can be induced in most liquids if cooling occurs rapidly enough. Although the vitrification of pure water requires cooling rates on the order of $10^{8\circ}$ C./min, the cytoplasm of cells is rich in proteins that enhance their vitrification tendency. However, cooling rates on the order of millions of degrees per minute are still required. The addition of cryoprotective agents (CPA) greatly decreases these prohibitively high cooling rates. Among the most commonly used are dimethyl sulfoxide (DMSO), glycerol, ethylene glycol (EG) and 1,2-propanediol (PROH). In general, for concentrations of CPA above 60% w/w, ice nucleation is avoided, allowing the solution to vitrify at any cooling rate. Unfortunately, such concentrations are extremely toxic to many types of cells and tissues, including oocytes. As a result, the CPA needed to vitrify must be decreased to a non-toxic level and the cooling rate must be increased to accommodate this reduction and allow vitrification.

Both slow-freezing and conventional vitrification techniques have associated disadvantages that can affect the viability of mammalian cells post cryopreservation. Effective methods are still needed for the cryopreservation of mammalian cells that combine the advantages of the two conventional approaches while avoiding their shortcomings.

SUMMARY OF THE INVENTION

The conventional techniques for the cryopreservation of mammalian cells are generally associated with disadvantages that detract from the potential use of the cells in clinical or research settings. For example, traditional slow-freezing techniques are associated with cell injury due to ice formation, high solute concentrations, and prolonged exposure to cryoprotectant. Vitrification avoids ice formation but requires a very high concentration of CPAs that is toxic to most mammalian cells. Thus, novel cryopreservation techniques that allow for the rapid cooling to achieve vitrification in the absence of high concentration of CPAs are needed.

We have discovered a novel method for cryopreservation of mammalian cells, including adult stem cells, embryonic stem cells, embryos, sperm, and oocytes, that combines the advantages of slow-freezing and vitrification while avoiding their shortcomings. Our newly discovered method includes the use of a thin-walled capillary tube made of a thermally conductive wall material that allows for rapid cooling of mammalian cells to a vitrified state in the absence of toxic levels of CPA and in the absence of ice formation. These features are advantageous because they allow for the passage of cells suspended in the media from a liquid to a super-cooled liquid to a vitrified state in the absence of ice formation and in the absence of toxic levels of CPAs. We have shown that this method can be used to cryopreserve mammalian cells, including but not limited to adult stem cells, embryonic stem cells, oocytes, sperm, embryos, zygotes, and other types of cells such as hepatocytes, while protecting the cells from injury, maintaining their viability, and, in the case of embryonic stem cells, maintaining their pluripotency. This method has the advantage of allowing any mammalian cell to be stored until it is needed under conditions that cause minimal, if any, adverse side-effects to the cell.

Accordingly, in one aspect, the invention features a method for cryopreserving a cell or cells. The method includes suspending the cell in a vitrification solution. The cell or cells can be added to the vitrification solution or the vitrification solution can be added to cell. The vitrification solution can be any solution that is appropriate for cryopreservation. Exemplary vitrification solutions can include phosphate buffered saline (PBS) or any physiological solution. The vitrification solution can be supplemented with additional components including but not limited to serum, proteins, penicillin/streptomycin, lipids, salts, formamide, methoxylated compounds, polymers (e.g., polyvinyl pyrrolidone and polyvinyl alcohol), cryoprotectants, and/or sugars. Optional ly, the mammalian cell in the vitrification fluid is emulsified into a droplet of vitrification solution surrounded by an immiscible biocompatible fluid, for example, oil. The cell in the vitrification solution is then placed in a capillary tube having a wall made of a material that is thermally conductive. The ratio of the thermal conductivity to the wall thickness for the capillary tube is at least 1,000, 5,000, 10,000, 100,000, 500,000, or higher. Desirably, the capillary tube is a microcapillary tube and the thermal conductivity is at least 0.2 W m$^{-1}$ K$^{-1}$, 5 W m$^{-1}$ K$^{-1}$, or at least 8 W m$^{-1}$ K$^{-1}$ or greater. The thermal conductivity of the capillary tube can also be substantially higher (e.g., 2×, 3×, 4×, 5×, 6×, 7×, 8×, 9×, 10×, 12×, 14×, 15×, 16×, 18×, 20×, 25×, 50× or greater) than the thermal conductivity of the vitrification solution. At least a portion of the capillary tube housing the vitrification solution and the mammalian cells is then exposed to a temperature less than or equal to −80° C., preferably less than or equal to −100° C., −196° C., or −205° C. Optionally, the method can also include shaking the housing, for example, at a frequency of at least 1.0 Hz-100 Hz, desirably more than 100 Hz. The cell in the vitrification solution in the capillary tube is then cooled at a rate of 30,000-100,000,000° C./minute, preferably equal to or greater than 100,000° C./minute, 200,000° C./minute, 350,000° C./minute, or 1,000,000° C./minute, or higher, where the cooling causes vitrification of the mammalian cell in the vitrification solution in the absence of ice formation.

The preferred capillary tube is a microcapillary tube that has a wall thickness of 1 to 100 µm, more desirably 7 to 14 µm, or 10 µm. The thickness of the wall will depend on the thermal conductivity of the wall material, such that the ratio of the thermal conductivity to the wall thickness for the capillary tube is at least 1,000, 5,000, 10,000, 100,000, 500,000, or higher.

The inner diameter of the microcapillary tube is generally 1 to 400 µM, more desirably 10 to 200 µm or the size of one cell, two cells, three cells or more.

The capillary tube can be made of any thermally conductive material including, but not limited to, plastic, glass, quartz, stainless steel, sapphire, gold, silver, copper, diamond, titanium, palladium, and platinum. In one embodiment, the capillary tube is a quartz microcapillary tube. In another embodiment, the capillary tube is a quartz microcapillary tube with a wall thickness of 10 µm and an inner diameter of 150 to 200 µm. In another embodiment, the outer surface of the capillary tube can be surface with such as microfins and coatings.

The vitrification solution can include at least one, two, three, or more cryoprotective agents (CPAs). The CPA can be any CPA known in the art including but not limited to sugar (e.g., sucrose, trehalose, raffinose, stachyose, and dextran), glycerol, polypropylene glycol, ethylene glycol, 1,2-propanediol, and DMSO. The CPA or combination of CPAs is desirably present at a concentration less than or equal to 4M, 3M, 2.5M, 2M, 1M, 0.5M, 0.3M, or less. The combination of CPAs can include any of these concentrations of each CPA. For example, one CPA can be present at a concentration of 2M, while the other is present at 0.5M or 0.3M. Examples of combinations of CPAs include 1,2-propanediol and a sugar or ethylene glycol and a sugar.

In one embodiment, the vitrification solution also includes at least one nanoparticle or microparticle. Exemplary nanoparticles or microparticles include a carbon or noble metal (e.g., gold, silver, titanium, palladium, platinum, and copper).

In one embodiment, the vitrification solution also includes at least one polymer or peptide (e.g., ice blocker) that inhibits ice nucleation and growth in the vitrification solution. Non-limiting examples of the polymer or peptide include polyvinyl alcohol, polyglycerol, and antifreeze proteins. Additional examples are known in the art.

The method can be used to cryopreserve any mammalian cell including an oocyte, sperm, embryonic stem cell, a stem cell, an embryo, a zygote, or any other type of cells. The mammal can be any mammalian cell type including human, murine, bovine, equine, porcine, or from a mammal that is an endangered or threatened species. Additional examples of cells and mammals are provided below.

By "capillary tube" is meant any small tube. Preferably, the capillary is a microcapillary tube. A microcapillary tube is a capillary tube that is on a sub-millimeter scale. Capillary tubes can be made of a variety of materials and in a variety of dimensions, which are specified herein.

By "cryoprotective agent," "cryoprotectant," or "CPA" is meant a compound used to slow or prevent ice nucleation, ice-crystal growth, ice formation, or any combination thereof. Cryoprotectants are generally agents with high water solubility and low toxicity. Included within this term are both permeating (e.g., glycerol, ethylene glycol, 1,2-propanediol, and DMSO) and non-permeating (e.g., sugars, dextran, polyvinyl pyrrolidone and hydroxyethyl starch) cryoprotectants. Non-limiting examples of cryoprotectants useful in the methods of the invention are ethylene glycol, glycerol, 1,2-propanediol, DMSO, and sugars (e.g., sucrose, trehalose, raffinose, stachyose, and dextran).

By "ice blocker" is meant a compound (e.g., a polymer or polypeptide) that prevents or inhibits ice nucleation and growth. Non-limiting examples of ice blockers include polyvinyl alcohol, polyglycerol, antifreeze proteins, and other polymer and peptides referred to in the art as ice blockers.

By "nanoparticle" is meant a particle having dimensions on the sub-micron scale range. Non-limiting examples of nanoparticles include gold, silver, copper, and carbon nanoparticles and nanotubes.

By "microparticle" is meant a particle having dimensions on the sub-millimeter scale. Non-limiting examples of microparticles include that of gold, silver, and other thermally conductive materials.

By "thermal conductivity" is meant the intensive property of a material that indicates its ability to conduct heat and is measured in W m$^{-1}$ K$^{-1}$. Thermal conductivity (k) is defined as the quantity of heat, Q, transmitted in time, t, through a thickness τ, in a direction normal to a surface of area A, due to a temperature difference, ΔT, under steady state conditions and when the heat transfer is dependent only on the temperature gradient. Thermal conductivity=heat flow rate distance/(area temperature difference) or $$k = \frac{Q}{t} \times \frac{\tau}{A \times \Delta T}.$$

For the capillary tubes of the invention, the wall material preferably has a high thermal conductivity.

By "high thermal conductivity" is meant a thermal conductivity greater than or equal to 5 W m$^{-1}$ K$^{-1}$, preferably greater than or equal to 8 W m$^{-1}$ K$^{-1}$.

By "substantially higher" is meant at least 2×, 3×, 4×, 5×, 6×, 7×, 8×, 9×, 10×, 12×, 14×, 15×, 16×, 18×, 20×, 25×, 50× or greater.

By "thermal diffusivity" is meant a property of a material that indicates a measure of the rate at which a temperature disturbance at one point in a body travels to another point and is measured in m$^2$ s$^{-1}$. Thermal diffusivity (α)=thermal conductivity/(density specific heat) or $$\alpha = \frac{k}{\rho \times c_p}.$$

By "specific heat" is meant the intensive property of a material that indicates its ability to absorb or hold heat and is measured in J kg$^{-1}$ K$^{-1}$. Specific heat is defined as the amount of heat in Joule required to increase 1 K or 1° C. of temperature in one kilogram of the material.

By "vitrification" is meant a process of converting a material into a glass-like amorphous solid which is free of any crystalline structure. Vitreous solidification occurs at the glass transition temperature (which is lower than the melting temperature, $T_m$, due to supercooling).

By "cryopreservation solution" or "cryopreservation media" is meant any solution or media which is used to cool cells, either by slow-freezing or vitrification.

By "vitrification solution" or "vitrification media" is meant a solution or a media which is mixed with one or more cells prior to vitrification. Vitrification solutions can include, for example, PBS or any physiological solutions. A vitrification solution can be supplemented with one or more components including, but not limited to, serum, proteins, penicillin/streptomycin, lipids, salts, formamide, methoxylated compounds, polymers (e.g., polyvinyl pyrrolidone and polyvinyl alcohol), cryoprotectants, and/or sugars.

By "supercooling" is meant the process of chilling a liquid below its freezing point without any ice formation.

By "ultra rapid cooling" is meant to cool at a rate higher than 10,000° C./minute.

We have discovered novel methods for the vitrification of mammalian cells while reducing the levels of CPAs, which are toxic to the cells at high levels. Such methods are advantageous because they improve the viability of the cells, which can then be used in a variety of research and clinical settings, for example, in assisted reproductive technology or for patients undergoing chemotherapy or radiation therapy or for cell-based therapeutics, which require the use of stem cells.

The present invention provides a number of advantages related to the cryopreservation of cells. For example, these methods may be generally applied to the preservation of any cell from any mammal. These cells may be stored in a cryogenic (e.g., less than or equal to −80° C.) state for any length of time until they are needed. Additionally, these cryopreservation methods can involve the use of relatively low concentrations of cryopreservation agents that cause minimal, if any, adverse side-effects in the cryopreserved cells.

Other features and advantages of the invention will be apparent from the following Detailed Description, the drawings, and the claims.

BRIEF DESCRIPTION OF THE DRAWINGS

FIG. 4A is a diagram of a temperature gradient microfluidic device in which individual cells within aqueous droplets smaller than 10 µl are vitrified via passage through a temperature gradient. Using such a device, the droplets may be cooled at a constant rate by moving at a constant speed through a linear drop in temperature. Alternatively, droplets can pass through a cooled metal block (FIG. 4B) through small passages, thereby increasing further the cooling rate in a continuous flow device. FIG. 4C is a diagram showing that filling a QMC with emulsion containing encapsulated cells in aqueous-CPA droplets should allow CPA levels to be reduced further than would be possible by filling with cell suspension alone.

FIG. 5A is a picture showing a comparison between the size of QMC (left) and OPS (right). This geometrical difference has consequences not only in the heat transfer efficiency but also in the probability of ice nucleation and growth. Also shown is a detail of the junction of the thermocouple inside the QMC (FIG. 5B).

FIG. 6A shows the thermal history for the OPS when filled with a 1.8 molar cryoprotectant solution quenched in liquid nitrogen and then warmed in a water bath at 37° C. A clear heat release peak is present during cooling as well as melting during warming. FIG. 6B shows the thermal history for QMC when filled with a 1.8 molar cryoprotectant solution quenched in liquid nitrogen and then warmed in a water bath at 37° C. Crystallization of water is not obvious during cooling, but melting is shown during warming. FIG. 6C shows the thermal history for OPS when filled with a 1.8 molar cryoprotectant solution quenched in slush nitrogen and then warmed in a water bath at 37° C. In this case, crystallization during cooling and melting during warming was not recorded. However, visual inspection reveals the presence of ice. FIG. 6D shows the thermal history for QMC when filled with a 1.8 molar cryoprotectant solution quenched in slush nitrogen and then warmed in a water bath at 37° C. The sample keeps its transparency over all the cooling-warming cycle, an indication of the capability of this approach to vitrify the studied solution.

FIG. 17A-17D depicts typical micrographs (10×) of the phase contrast image (FIG. 17A) and the fluorescence detection of Oct-4 expression (FIG. 17B) and SSEA-1 staining (FIG. 17C) of two representative cell colonies. Also shown is the histochemical staining of the enzyme alkaline phosphatase (FIG. 17D) at low magnification (4×). The inset in FIG. 17D shows a representative colony stained with alkaline phosphatase at high magnification (10×).

DETAILED DESCRIPTION

Figure 1:
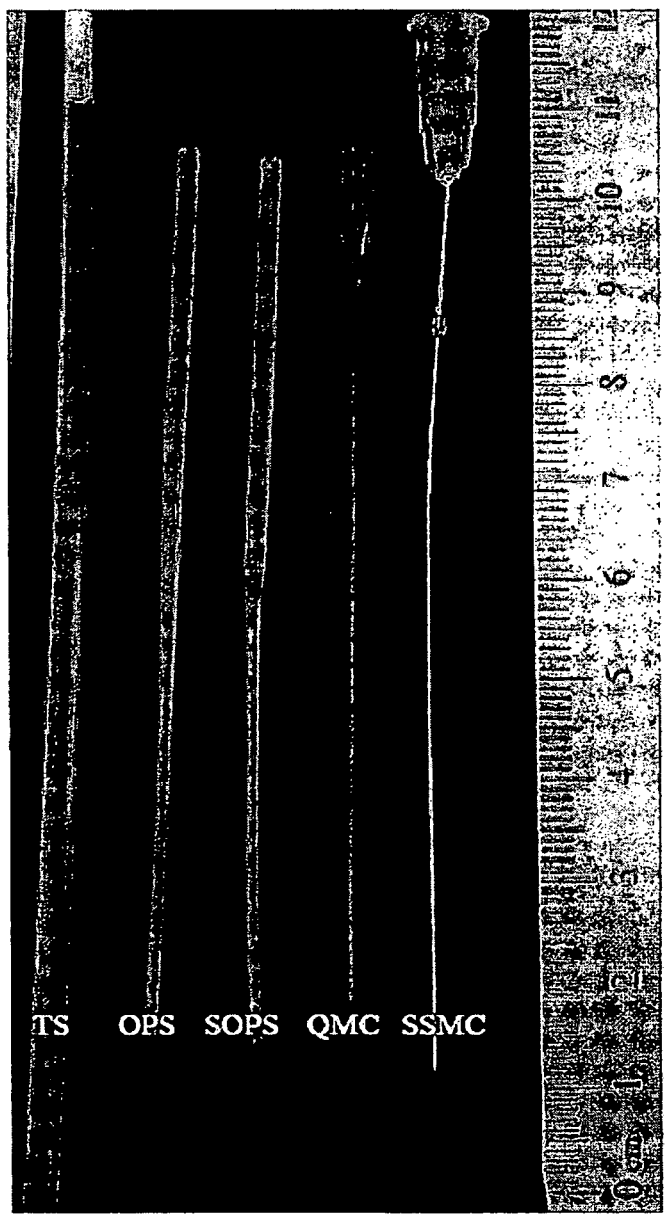
FIG. 1 shows a comparison of devices including the traditional straw (TS), the open pulled straw (OPS), the superfine open pulled straw (SOPS), the quartz microcapillary (QMC), and stainless steel (SSMC) micro-capillary. The QMC and SSMC devices have a diameter just slightly larger than that of a human oocyte.

We have discovered methods for the cryopreservation of mammalian cells that combines the advantages of the slow-freezing and vitrification approaches while avoiding their shortcomings. For cryopreservation, the mammalian cells are placed in a vitrification solution that is then placed in the capillary tube. The capillary tubes used in the methods of the invention include a wall that is made of a thermally conductive material, where the ratio of the thermal conductivity of the wall to the wall thickness is at least 1,000, 5,000, 10,000, 100,000, 500,000, or higher. The solution in the capillary tube is then exposed to temperatures equal to or less than −80° C., preferably equal to or less than liquid nitrogen or slush nitrogen temperature (e.g., −196° C. or −205° C., respectively) and the vitrification solution containing the mammalian cells is cooled at a rate greater than or equal to 30,000-100,000,000° C./minute, preferably 100,000° C./minute, 200,000° C./minute, 350,000° C./minute, 1,000,000° C./minute, or higher. The exposure of the highly conductive tube with the low thermal mass allows for vitrification of the solution in the absence of ice formation. Cyroprotectants can also be added to the vitrification solution to further prevent ice formation. The present methods are advantageous over the traditional methods for cryopreservation because they achieve rapid cooling in the absence of ice formation and toxic concentrations of cryoprotectants, both of which greatly increase the viability and usability of the cryopreserved cell after it has been warmed. Cells The present invention can be used for the cryopreservation of any type and any species of mammalian cells. For example, the method can be used to cryopreserve oocytes or sperm in assisted reproductive technology or for patients undergoing chemotherapy or radiation therapy. The method can also be used for the cryopreservation of stem cells, such as embryonic stem cells, or other cells, which can then be used as the basis of stem cell-based therapies, cell transplantation, tissue engineering, and regenerative medicine.

The method can also be used to cryopreserve oocytes or sperm from an animal that is rare or at risk of becoming extinct for future use in assisted reproductive technologies for the preservation of the species. The method can further be used for animal husbandry purposes (e.g., the breeding and raising of animals), for example, for the cryopreservation of embryonic stem cells, gametocytes, oocytes, or sperm from animals such as cows, pigs, and sheep.

Cell types that may be cryopreserved using the compositions and methods of the present invention include, for example, differentiated cells, such as epithelial cells, cardiomyocytes, neural cells, epidermal cells, keratinocytes, hematopoietic cells, melanocytes, chondrocytes, B-cells, T-cells, erythrocytes, macrophages, monocytes, fibroblasts, or muscle cells; and undifferentiated cells, such as embryonic, mesenchymal, or adult stem cells. Additional cell types that can be cryopreserved using the methods of the invention include gametocytes, oocytes, sperm, zygotes, and embryos. The cells can be haploid (DNA content of n; where "n" is the number of chromosomes found in the normal haploid chromosomes set of a mammal of a particular genus or species), diploid (2 n), or tetraploid (4 n). Other cells include those from the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

The cells may be from a human or non-human mammal, for example Cercopithecoidea family, Hominoidea superfamily, *Canis familiaris, Felis catus, Cricetidae* spp., *Equus* spp. (e.g., *Equus caballus, Equus assinus*), Equidae family, *Bos taurus, Bos indicus*, Bovidae family, Camelidae family, *Bubalus bubalis, Capra aegagrus hircus*, Cervidae family, Cervinae family, *Ovis aries, Ovis canadensis, Capra hircus, Sus scrofa* domestica, *Mesocricetus* spp., *Mustela vison, Cavia porcellus, Meriones unguiculatus, Chinchilla laniger, Rattus norvegicus, Rattus* spp., *Mus musculus*, Leporidae family, *Oryctolagus cuniculus, Kobus* spp., *Gallus* spp., *Meleagria gallopavo, Anatidae* spp., *Mustela putorius, Columba domestica, Columba livia, Numida meleagris, Ornithorhynchus anatinus, Pavo cristatus, Bison* spp., *Struthio* spp., *Lama glama, Rhea* spp., *Dromiceius* spp., *Lama pacos, Rangifer tarandus, Bos grunniens, Camelus bactrianus, Camelus dromedarius*), and any endangered or threatened species (e.g., those species identified by the U.S. Fish and Wildlife Service (USFWS) Threatened and Endangered Species System (TESS)).

The cells are prepared for cryopreservation using techniques known in the art and described herein. Generally, the mammalian cells are obtained using art known techniques and maintained in media appropriate for the cell type. The cells are then mixed with a vitrification solution. The cells can be added to the vitrification solution or the vitrification solution can be added to the cells. Alternatively, the cell media is modified to include all the components needed for vitrification. The concentration of the cells in the vitrification solution varies widely depending on the cell type. For example, for oocytes, the concentration of cells can be low, for example, as low as <1 cell/ml, while for stem cells, the cell concentration can be higher than 10M/ml. The exact concentration can be determined by the skilled artisan for the particular cell type.

The vitrification solution can include any physiologic solution such as 1× phosphate buffered saline (PBS), FHM (a flush hold Hepes-buffered medium from Specialty Media, Lavallette, N.J.), or a cell media, for example, a stem cell culture medium that includes Knockout DMEM+15% Knockout Serum Replacement (Invitrogen, Carlsbad, Calif.) containing 1000 U/ml Leukemia Inhibitory Factor (Chemicon, Temecula, Calif.). The vitrification solutions is desirably supplemented with one or more components including, but not limited to, serum, proteins, penicillin/streptomycin, lipids, salts, formamide, methoxylated compounds, polymers (e.g., polyvinyl pyrrolidone and polyvinyl alcohol), cryoprotectants, and/or sugars.

The cells are then loaded into a capillary tube, for example by capillary action or using a syringe, and the tube is then exposed to temperatures less than or equal to −80° C., preferably less than or equal to the temperature of liquid nitrogen or slush nitrogen temperature (e.g., −196° C. or −205° C., respectively), and the vitrification solution containing the mammalian cells is cooled at a rate equal to or greater than 30,000-100,000,000° C./minute, for example, 100,000° C./minute, 200,000° C./minute, 350,000° C./minute, or even 1,000,000° C./minute. For example, the tube can be plunged into liquid nitrogen or slush or slurry nitrogen; optionally with shaking, to cause vitrification of the cell and the vitrification solution in the absence of ice formation. The vitrified cells in the vitrification solution can then be stored at a temperature less than or equal to −80° C., preferably equal to or less than liquid nitrogen temperature for any desired amount of time (e.g., up to and beyond 10 years) until the cell is needed. The cells are then warmed, using any number of techniques known in the art, for example, by plunging the tube into a 1×PBS solution at 20-37° C., preferably room temperature, optionally with shaking and optionally supplemented with sugar or other CPAs. After warming, the cells are generally washed and treated as needed for the research or clinical applications. It will be clear to the skilled artisan the exact conditions and media that are used for culturing the cells before, during, and after warming. Exemplary protocols are provided in the examples below.

Capillary Tubes

The devices used in the methods of the present invention include capillary tubes with various dimensions and materials. Generally, the capillary tube is a microcapillary tube and is made of a wall material that is thermally conductive. Desirably, the microcapillary tube has thin walls (e.g., about 1 to 100 μm), where the ratio of thermal conductivity to wall thickness is at least 1,000, 5,000, 10,000, 100,000, 500,000, or higher. Desirably, the microcapillary tube has a relatively small diameter (e.g., from 1 to 400 μm). In one example, the microcapillary tube is a quartz microcapillary tube (QMC), commercially available, for example from Charles Supper Co. (Natick, Mass.) or Wolfgang Muller Glas Technik (Germany). The combination of a highly conductive material with thin walls and a relatively small diameter of the tube allows for rapid cooling in the absence of ice formation or toxic levels of CPAs.

Material

The vitrification devices of the present invention can be made of any thermally conductive material. Preferably, the material has a thermal conductivity greater than 5 W m$^{-1}$ K$^{-1}$, preferably greater than or equal to 8 W m$^{-1}$ K$^{-1}$. Examples of thermally conductive materials useful for the capillary tubes in the methods of the invention include plastics, glass, quartz, sapphire, gold, copper, silver, diamond, titanium, palladium, platinum, and stainless steel.

As described in detail below, the ratio of thermal conductivity (in W m$^{-1}$ K$^{-1}$) to the wall thickness (in meter) for the capillary tube wall should be at least 1,000, 5,000, 10,000, 100,000, 500,000, or higher. A microcapillary tube having a wall material that has a lower thermal conductivity (e.g., 0.2 W m$^{-1}$ K$^{-1}$) will generally have a much thinner wall in order to achieve the ratios of thermal conductivity to the wall thickness described above. Table 1, below provides the thermal conductivity of exemplary wall materials.

TABLE 1

A list of the thermal properties used in the thermal model for thermal analysis

| Materials | Density, kg/m³ | Specific heat, J kg⁻¹ K⁻¹ | Thermal Conductivity, W m⁻¹ K⁻¹ |
|---|---|---|---|
| Solution | 1022 | 3800 | 0.54 |
| Plastics | 1200 | 1500 | 0.2 |
| Glass | 2200 | 850 | 0.8 |
| Quartz | 2649 | 710 | 8 |
| Sapphire | 3970 | 419 | 27.2 |
| Gold | 19300 | 129 | 320 |
| Copper | 8920 | 385 | 385 |
| Silver | 10490 | 232 | 406 |
| Diamond | 3500 | 502 | 1000 |

Preferably, the thermal conductivity of the capillary wall material is substantially greater (e.g., 2×, 3×, 4×, 5×, 6×, 7×, 8×, 9×, 10×, 12×, 14×, 15×, 16×, 18×, 20×, 25×, 50× or greater) than the thermal conductivity of the vitrification solution. For example, a quartz tube having a thermal conductivity of 8 W m⁻¹ K⁻¹ has a thermal conductivity that is approximately 15 times that of a vitrification solution having a thermal conductivity that is generally less than 0.6 W m⁻¹ K⁻¹, the thermal conductivity of water at room temperature.

In one embodiment, the capillary tube wall material is quartz, which is transparent and allows for real time monitoring of vitrification. However, materials that are not transparent, such as stainless steel, but that are thermally conductive can also be used.

Dimensions

We have discovered that the cooling rate increases in a strong nonlinear fashion with the decrease of the inner diameter when either plastic or quartz are used as the material for the capillary tube. The increases in the cooling rate are particularly pronounced when the inner diameter of the capillary tube is less than 0.4 mm. The cooling rate also increases significantly with the decrease of wall thickness and this effect is also more apparent when the inner diameter is less than 0.4 mm for both plastic and quartz. (See FIGS. 11A and 11B.) The methods of the invention therefore feature capillary tubes, preferably microcapillary tubes, that have thin walls and a small inner diameter as these are better suited for achieving a high cooling rate.

Traditional cryopreservation devices used in the art include the traditional straw (TS) and the open pulled straw (OPS) and the cooper grid. The dimensions of these devices and the microcapillary tubes of the invention are compared in Table 2, below.

TABLE 2

A list of reported and potential vitrification devices and their dimensions

| Materials | OD, mm | ID, mm | Thickness, mm |
|---|---|---|---|
| Traditional straw (TS) | 2 | 1.7 | 0.15 |
| Open pulled straw (OPS) | 0.95 | 0.8 | 0.075 |
| Grid (0.5 µl) | 1.24 | N/A | N/A |
| Quartz micro-capillary (QMC) | 0.2 | 0.18 | 0.01 |
| Stainless steel micro-capillary 1 (SSMC1) | 0.203 | 0.165 | 0.019 |
| Stainless steel micro-capillary 2 (SSMC2) | 0.178 | 0.14 | 0.019 |

In preferred embodiments of the invention, the microcapillary tube has a wall thickness ranging from about 1 to 100 µm, preferably 5 to 25 µm, and most preferably 10-20 µm. The inner diameter of the microcapillary tube preferably ranges from about 1 to 400 µm, preferably around 150 to 180 µm, or comparable to the size of a human oocyte (approximately 120 µm on average). Such dimensions can be optimized for any wall material and for any cell type, for example, if the diameter of the cell itself is larger or smaller. The diameter of the tube is generally at least 5% bigger than the size of the cell to be cryopreserved. The thickness and diameter of the portion of the capillary tube that contains the solution are roughly uniform, although it is not necessary and often depends on the manufacturing process used to make the microcapillary tube. For example stainless steel microcapillary tubes are made from a flat sheet of stainless steel, which is roll formed to precise dimensions and then weld or fused together with generally a laser. This process generally produces a tube with a uniform diameter. The open pulled straw and the quartz microcapillary are manufactured by heating and then pulling a bigger plastic straws and quartz tubes to the desired dimensions, respectively. This process results in a tube that can vary in diameter, for example being wider at one end of the tube (see FIG. 1).

Thermal Properties

As described above, the capillary tube includes a wall made of a thermally conductive material. The desired thermal conductivity of the wall material is also dependent on the thickness of the wall material. For example, the following relationship should hold if the wall of the capillary tube were rolled out flat:

$$k/\tau \gg h$$

where $k$ is thermal conductivity, $\tau$ is wall thickness, and $h$ is boiling heat transfer coefficient. The boiling heat transfer coefficient (h) varies from 110-11,000 W m⁻² K⁻¹ (Randall F. Barron. *Cryogenic Heat Transfer*, UK: Taylor Francis, 1999). For the capillary tubes of the invention, a forced convective fluid flow in addition to boiling is created when rapidly plunging the capillary tube into cryogenic fluid. The boiling heat transfer coefficient should generally be more than 5,000 W m⁻² K⁻¹. If we increase the boiling heat transfer coefficient by 10 times (10×110=1,100), the following equation could be used to describe the relationship between the wall thickness and the thermal conductivity of the wall materials of the invention (using 1,000 as a rounded number for 1,100):

$k/\tau > 1,000$ (W m⁻² °C.⁻¹). In preferred embodiments, using a highly conductive material with a small wall thickness, for example, $k/\tau \geq 500,000$ (W m⁻² °C.⁻¹).

Figure 3:
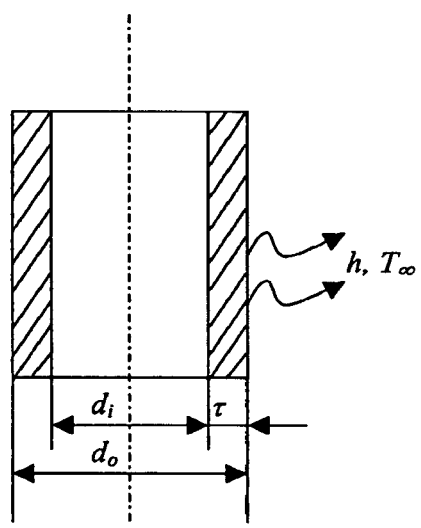
FIG. 3 depicts the parameters which determine the cooling rate including the inner diameter ($d_i$), the outer diameter ($d_o$), the wall thickness ($\tau$), thermal properties of the wall material, the boiling heat transfer coefficient between the outside wall and the cryogenic fluid (e.g., liquid/slush/slurry nitrogen) and the temperature of the cryogenic fluid ($T_\infty$).

The relationship between the wall thickness, thermal conductivity, and the inner diameter of the capillary tube can be further described by understanding the thermal resistance of the tube as described in detail below (see FIG. 3).

Parameters Defined by the Wall

In this part, the heat transfer inside the vitrification solution is assumed to be fast enough so that its thermal resistance is negligible. Therefore, only the thermal resistance of a hollow cylindrical wall is considered, which can be calculated based on the outside wall as:

$$R_w = \frac{d_o}{k_w} \ln\left(\frac{d_o}{d_i}\right) \quad (1)$$

where R is thermal resistance, k is thermal conductivity, d is diameter, the subscripts w, o, and i denote wall, outer and inner, respectively.

The thermal resistance of the boiling heat transfer between the outside wall and cryogen is:

$$R_b = \frac{1}{h} \tag{2}$$

where h is the boiling heat transfer coefficient between the outer surface of the cylinder and the surrounding liquid nitrogen. The thermal resistance of the wall should be much less than that of the boiling process so that the thermal barrier of the wall could be negligible:

$$R_w \ll R_b \tag{3}$$

Therefore, the following relationship can be used to define the thermal and geometrical parameters of the wall:

$$\frac{d_o}{k_w} \ln\left(\frac{d_o}{d_i}\right) \ll h^{-1} \tag{4}$$

If we set 10% as the criterion for much-less in equation (4), the following relationship for inner diameter, outer diameter (or wall thickness, $d_o = d_i + 2\tau$), and the thermal conductivity of the wall material for the capillary tubes can be used.

$$\frac{d_o}{k_w} \ln\left(\frac{d_o}{d_i}\right) \leq 0.1 h^{-1} \tag{5}$$

Parameters Defined by the Vitrification Solution

In this part, the heat transfer through the wall is assumed to be fast enough so that its thermal resistance is negligible. Therefore, only the thermal mass of the vitrification solution is considered. First, we consider the case for which the thermal non-homogeneity in the vitrification solution is negligible and therefore, the Biot number (Bi) should be less than 0.2 as follows:

$$Bi = \frac{h(0.25 d_i)}{k_m} \leq 0.2 \tag{6}$$

where the subscript m denotes cell-carrying vitrification solution. Therefore, the diameter of the micro-capillary should satisfy the following requirement:

$$d_i \leq \frac{0.8 k_m}{h} \tag{7}$$

The thermal conductivity of the medium could be assumed the same as water 0.6 W/(m K). Therefore, the following relationship should hold:

$$d_i \leq 0.48 h^{-1} \tag{8}$$

When we lump the 1D medium space, the time dependent average temperature in the medium can be calculated as follows:

$$\frac{T - T_\infty}{T_0 - T_\infty} = \exp\left[-\left(\frac{4h/(\rho c_p)_m}{d_i}\right) t\right] \tag{9}$$

where ρ is density, $c_p$ is specific heat, and t is time. The subscripts m, o, and ∞) represent cell carrying medium, initial time, and liquid nitrogen, respectively. Since the glass transition temperature of a cryopreservation medium generally should be higher than −130° C., the target temperature for cooling cells is −130° C. as quickly as possible. According to equation 9, the following relationship holds:

$$\exp\left[-\left(\frac{4h/(\rho c_p)_m}{d_i}\right) t\right] = \frac{-130 - (-196)}{20 - (-196)} = 0.306 \tag{10}$$

Taking natural logarithm on both sides of the above equation, the equation is as follows:

$$\frac{4h/(\rho c_p)_m}{d_i} t = 1.186 \tag{11}$$

If we want to cool the cell carrying medium from 20° C. to −130° C. within half a second (t≤0.5 s, CR≥1.8 10^4° C./min), the following relationship should hold:

$$d_i \geq 1.687 h/(\rho c_p)_m \tag{12}$$

The density and specific heat of the medium are around 1000 kg/m³ and 4200 J/(kg K), respectively. Therefore, the following relationship should approximately hold:

$$d_i \leq 4.02 \times 10^{-7} h \tag{13}$$

Putting equations 8 and 13 together, the inner diameter should satisfy the following requirement:

$$d_i \leq \min\{0.48 h^{-1}, 4.02 \times 10^{-7} h\} \tag{14}$$

SUMMARY

According the above discussion, the geometric and thermal parameters should follow equations 5 and 14, which are shown together below:

$$\frac{d_o}{k_w} \ln\left(\frac{d_o}{d_i}\right) \leq 0.1 h^{-1} \tag{5}$$

$$d_i \leq \min\{0.48 h^{-1}, 4.02 \times 10^{-1} h\} \tag{14}$$

The pool boiling heat transfer coefficient in liquid nitrogen ranges from 110 (film boiling)-11,000 (nucleate boiling) W/(m² K). Generally, the coefficient for the methods of the invention is greater than or equal to 1000 W/(m² K). Using h=1000 W/(m² K), the two geometric parameters including the inner diameter and the wall thickness [τ=0.5*($d_o - d_i$)] could be defined by the following two equations:

$$\frac{d_o}{k_w} \ln\left(\frac{d_o}{d_i}\right) \leq 1 \times 10^{-4}, m^2 K W^{-1} \tag{5*}$$

$$d_i \leq 4.02 \times 10^{-4}, m \tag{14*}$$

It should be noted that the above parameters can be modified by assuming a different boiling heat transfer coefficient.

Cooling Rate

As described above, traditional methods for cryopreservation include slow freezing, or cooling at a rate of <50° C./minute, and vitrification, or cooling at a rate of <25,000°

C./minute (Vajta, G. et. al. Molecular Reproduction and Development 51: 53-58, 1998). The methods of the present invention include the use of a cooling rate greater than or equal to 30,000° C./minute, which allows for vitrification in the absence of ice crystal formation. The combination of the thermally conductive wall material with a thin wall, as described above, allows for this ultra-fast cooling rate to be achieved. The cooling rates for various art known cooling devices are compared to the cooling rates of the microcapillary tubes of the invention in FIG. 13.

In the present invention, the capillary tubes, preferably microcapillary tubes, are exposed to a low temperature, for example by plunging into liquid nitrogen or slush nitrogen and cooled at a rate that is greater than or equal to 30,000-100,000,000° C./minute, preferably 50,000° C./minute, 100,000° C./minute, 200,000° C./minute, 350,000° C./minute, or a rate that is greater than or equal to 1,000,000° C./minute.

Cryoprotective Agents (CPAs)

As described above, the present methods feature the cryopreservation of mammalian cells by vitrification in the absence of ice formation or toxic levels of cryoprotectants. The vitrification solution can include CPAs, which are preferably included at concentrations less than 4M, less than 3M, 2M, 1M, or 0.5M. The CPAs can be permeating or non-permeating or a combination of permeating and non-permeating. Exemplary threshold concentrations of CPAs as a percentage of volume are described in detail in the examples below.

Non-limiting examples of CPAs that are useful in the methods of the invention include sugar, polypropylene glycol, ethylene glycol, 1,2-propanediol (PROH), glycerol, and DMSO. Desirably the sugar is any one of the following: sucrose, trehalose, raffinose, stachyose, and dextran. Exemplary sugars and the concentration ranges for such sugars are described in U.S. Pat. Nos. 6,673,607 and 7,094,601, herein incorporated by reference.

CPAs can be added to the vitrification solution as a single agent or as a combination of one or more agents. For example, 2M ethylene glycol or 1,2-propanediol (PROH) can be supplemented with 0.5 to 2M sugar to produce a synergistic effect. For example, a combination of ethylene glycol and a sugar or a combination of PROH and a sugar can be used. In one example, 2M PROH and 0.5 M trehalose are added to the vitrification solution. In another example, 0.3M sucrose and 1.5M PROH is used. The combination of a permeating and non-permeating CPA allows for a lower intracellular concentration of CPA, since the non-permeating CPA does not enter the cell. For example, in the 2M PROH and 0.5 M trehalose example described above, the intracellular concentration of CPA would be 2M since trehalose is not permeable to the plasma membrane of mammalian cells.

Nanoparticles and Microparticles

The vitrification solution can further include nanoparticles or microparticles or both. The addition of nanoparticles, microparticles, or nanotubes are thought to enhance the thermal conductivity of the vitrification solution. Examples of such nanoparticles or micro particles include particles having carbon or a noble metal, such as gold, silver, titanium, palladium, platinum, or similar particles thereto. Examples of such nanoparticles and/or microparticles and/or nanotubes may include, but are not limited to, carbon or noble metals, e.g., gold, silver, titanium, palladium, platinum, and copper.

In one aspect of the invention, the nanoparticles are present in the vitrification solution in an amount up to 99%, 50%, 25%, 20%, 10%, 5% or lower, based on the total weight of the solution. In another aspect of the invention, the microparticles are present in the vitrification solution in an amount up to 99%, 99%, 50%, 25%, 20%, 10%, 5%, based on the total weight of the solution. It has been shown that the presence of a small fraction (<1% vol) of nanoparticles in a solution can increase the thermal conductivity of the solution up to more than 200% (Choi et al., *Applied Physics Letter* 79: 2252-2254, 2001; Eastman et al., *Applied Physics Letter* 78: 718-720, 2001).

Surface Techniques

The outer surface of the capillary tubes can be treated to enhance the boiling heat transfer coefficient on the boundary between the cryogenic fluid/slush/slurry (i.e., liquid nitrogen or its slush) and capillary. Such techniques include microfins and surface coating. Microfins can increase the surface to volume ratio to enhance heat transfer. The use of such coatings can, for example, reduce the bubble formation or bubble attachment on the surface and hence enhance heat transfer between the cryogenic fluid/slush/slurry and capillary tube.

Ice Blockers

Ice blockers can also be included in the vitrification solution. Non-limiting examples of ice blockers include polymers and peptides having properties that inhibit ice nucleation and growth within the medium or similar polymers and peptides thereto. Examples of such polymers and peptides may include, but are not limited to, polyvinyl alcohol, polyglycerol, antifreeze proteins, and other polymer and peptides referred to in the art as ice blockers.

Cooling the Cells

The methods of the invention include exposing the capillary tube housing the vitrification solution and the mammalian cells to a temperature equal to or less than −80° C. (dry ice temperature), preferably less than or equal to liquid nitrogen temperature or −196° C. or slush nitrogen (−205° C.), which is a mixture of liquid and solid nitrogen. Generally, the capillary tube will be plunged into the cryogenic fluid/slush/slurry, for example, the liquid or slush nitrogen. Optionally, the method can include shaking the capillary tube at a frequency of about 1.0 Hz or higher while it is being exposed to the cryogenic temperatures (e.g., less than or equal to −80° C.).

Encapsulation in Microdroplets

In another aspect, the cells in the vitrification solution are emulsified into a droplet of the vitrification solution surrounded by an immiscible biocompatible fluid, including but not limited to oil.

The droplet can range in size from 10 µl to below 200 picoliters. Desirably, the droplet is less than 200 picoliters or about a 70 µm sphere. The oil may be replaced with other biocompatible immiscible fluids. The droplet may be generated using pipettes, nested capillaries or more sophisticated droplet generators, including but not limited to sprayers and microfluidics. The encapsulation can be done using a microfluidic device or a homogenizer.

The microfluidic generation of mono-disperse emulsions containing aqueous droplets in a continuous phase of oil are created by pushing an aqueous fluid through a small rectangular channel towards a junction with one or two similar channels where it meets an immiscible fluid (such as oil). Provided that the walls of the channels are wetted preferentially by the oil (typically achieved by ensuring hydrophobicity), the aqueous phase will be surrounded so that water droplets break from the aqueous stream in a regular fashion, creating the emulsion. Droplet size can then be controlled by varying the geometry of the junction between immiscible phases as well as the flow rates of both the oil and aqueous streams.

Such microfluidic devices can be used to entrap the individual cells within aqueous droplets smaller than 200 μm (4.2 nL) in diameter and desirable less than 200 picoliters or about a 70 μm sphere, separated from one another by an immiscible continuous phase. This encapsulation can be used to further enhance vitrification at any given cooling rate while simultaneously allowing the use of lower and less-toxic CPA concentrations in the vitrification solutions. While not wishing to be bound by theory, encapsulating the cells in a micro droplet is advantageous because an event which occurs randomly in space and time, such as homogeneous nucleation, will take longer to happen in a confined space and the chances of finding heterogeneous nucleating particles in a tiny droplet are vanishingly small.

Figure 4:
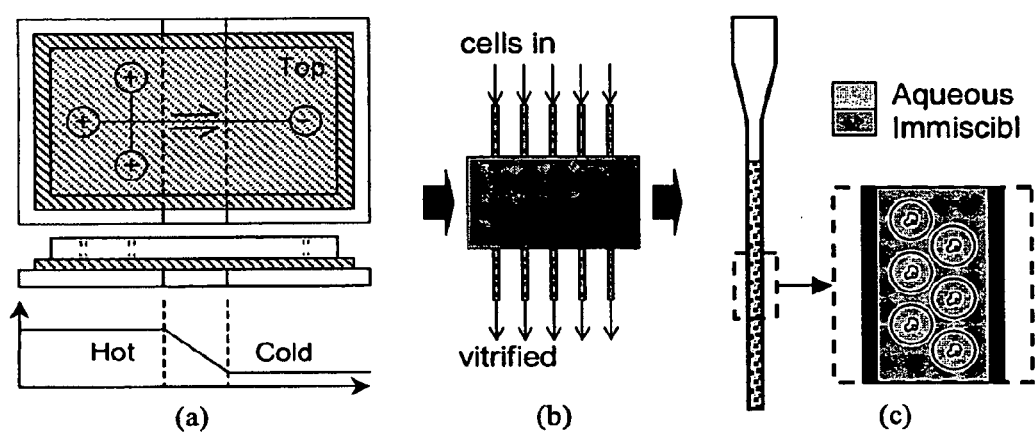
FIGS. 4A-4C show various embodiments of droplet vitrification technique.

For the encapsulation methods, microfluidic devices using techniques for microfluidic generation of monodisperse inverse emulsions can be extended with the ability to specify cooling rate on-chip by placing the microfluidic device atop a surface with a linear temperature gradient, such as a directional freezing stage like the GS350 from Linkam will be used (FIG. 4A). Such microscope stages provide a linear temperature gradient across a thin section of optically clear material by sandwiching it between two temperature-controlled blocks of material with high thermal conductivities. This linear drop in temperature from one side of the sandwich to the other, across the inner clear layer, allows a flat object placed on top of the stage to experience the same variation in temperature. The microfluidic device could then be observed microscopically in the region where cell-containing droplets, suspended within the immiscible continuous phase, cool as they travel within the microfluidic channels from the high temperature zone to the low temperature zone, where they should become vitrified in the process. The cooling rate can be additionally modulated, if desired, by fluid velocity, or simply by rotating the device so that the droplets take longer to cross the temperature gradient. The use of such a microfluidic device will also allow more complex cooling cycles to be developed, for example, if a multistep protocol is desired. In one example, a channel that has several kinks as it crosses the gradient zone can be used to allow for a slow initial cooling rate followed by rapid cooling at lower temperatures. Similarly, rewarming could be accomplished by routing the stream of droplets back to the high temperature zone on-chip. In addition to allowing continuous cellular vitrification, this would provide a powerful platform with which to further modify the technique.

Additional embodiments are depicted in FIG. 4B and include the use of a large cooled metal mass with several passages that carry emulsion through it, allowing even faster arrival at cryogenic temperature, but at a non-constant cooling rate. Notably, this would not be possible without droplets, since aqueous fluid will become impossible to pump after vitrification whereas vitrified droplets can continue to travel through these passages as long as the immiscible continuous phase remains pumpable.

Additionally, the use of cellular encapsulation within aqueous droplets will enhance the benefits of extremely rapid cooling as described for the methods herein using the capillary tubes of the invention by increasing the efficiency at any particular CPA level (FIG. 4C). This would involve filling the capillary tube of the invention (e.g., the quartz microcapillary tube) with the emulsion of cell-containing aqueous droplets suspended within an immiscible fluid. The benefit follows from the expectation that the probability of nucleation occurring anywhere within a capillary tube of the invention (e.g., a quartz microcapillary tube) filled with vitrification solution will be approximately equal to the sum of the probabilities of nucleation within all of the droplets that alternatively fill the same capillary, and since ice does not propagate from one droplet to another, the chances of any given cell achieving vitrification can become much higher for the same CPA levels with micro-encapsulation of cells into their own isolated micro-environments.

Viability of Cryopreserved Cells

When desired, the cryopreserved mammalian cells of the invention can be warmed, using methods known in the art or described herein. For example, the capillary tube can be plunged into a 1×PBS solution at 20-37° C., preferably room temperature, optionally with shaking and optionally supplemented with sugar or other CPAs. After warming, the cells are generally washed, suspended in the appropriate media and treated as needed for use in research or clinical applications. For example, embryonic stem cells can be plated and passaged using techniques known in the art. Oocytes are generally cultured in droplets of media immersed in oil. It will be clear to the skilled artisan the exact conditions and media that are used for culturing the cells before and after cryopreservation.

There are various tests known in the art to determine the viability and function of the cells after warming and these tests are dependent on the cell type and the desired use of the cell. For example, for ES cells that are to be used for cell-based therapeutics, maintenance of pluripotency is very important. The pluripotency of the ES cells can be tested using art known methods, including, for example, Oct4-GFP expression, elevated alkaline phosphatase expression, and SSEA-1 surface glycoprotein expression. The ability of cells to attach efficiently is another assay for the viability and usability of many cells. Attachment assays are known in the art and described herein. Proliferation assays can also be used to determine if the attached cells can proliferate as expected after cryopreservation. Attachment and proliferation efficiency can be compared to control cells, which have not undergone cryopreservation. For cryopreservation of zygotes, cleavage rates can be determined after cryopreservation and compared to control groups to determine if there has been any cellular damage during the cryopreservation process. The viability of oocytes can be determined by examination of the morphological characteristics of the cells following cryopreservation. Morphologically viable oocytes exhibits intact zona pellucida and plasma membrane and refractive cytoplasm, while non-viable oocytes appear degenerated when visualized under a light microscope. The ultimate criterion for oocyte viability and function is their capability to be fertilized by healthy sperm in vitro and in vivo, followed by cleavage, blastocyst, and/or hatching or development of the fetus.

The assays for cell viability, function, and usability can also be used to test parameters for the cryopreservation methods described herein. For example, variations in CPAs or CPA concentrations or in cooling rates or capillary tube materials or dimensions can readily be tested on cells and their effects on cell viability, function, and usability can be tested using any of the methods described herein or known in the art.

EXAMPLES

Example 1

Thermal Performance of Open Pulled Straws and Quartz Micro-Capillaries for Vitrification Three major factors that limit the cooling rate in the OPS include: the large thermal mass of the sample as a result of the large inner diameter of the OPS, the limited thermal conductivity of the container walls as a consequence of its material and thickness, and the formation of a vapor layer around it as a result of the nitrogen boiling when in contact with the relatively hot sample (Lidenfrost effect)(Cowley et al., Biodynamica 8:317-329, 1961; Steponkus et al., Nature 345:170-172, 1990). Therefore, as described above, there is still room for improved heat transfer, including reducing the inner diameter ($d_i$) of the straws and optimizing the material the straw is made from to reduce the wall thickness (t) and increase the thermal conductivity (FIG. 3).

In addition to optimizing the sample container, alterations in the cryogenic liquid can also increase the desired cooling rates. The use of propane for plunging has been explored elsewhere (Cowley et al., supra) with some reported drawbacks due to the possible permeability of the cells to this molecule. Instead, a more desirable approach is the utilization of slush nitrogen in order to reduce the insulating vapor layer which forms on the surface on the sample when plunged from room temperature into liquid nitrogen (Mazur et al., Cryobiology 30:45-73, 1993).

With these improvements in mind, the capability of quartz micro-capillaries (QMC), commonly used for X-ray diffraction, plunged in a two-phase slush nitrogen, was compared to the thermal performance of the conventional OPS. The reduced inner diameter of these capillaries (still compatible with human oocyte dimensions), the thinness of the capillary walls, and the large thermal conductivity of the quartz when compared with the PVC of the OPS, made in principle these capillaries ideal containers for human oocyte cryopreservation, avoiding the aforementioned drawbacks of other methods.

Materials and Methods

Open Pulled Straws and Quartz Micro-Capillaries

Figure 5:
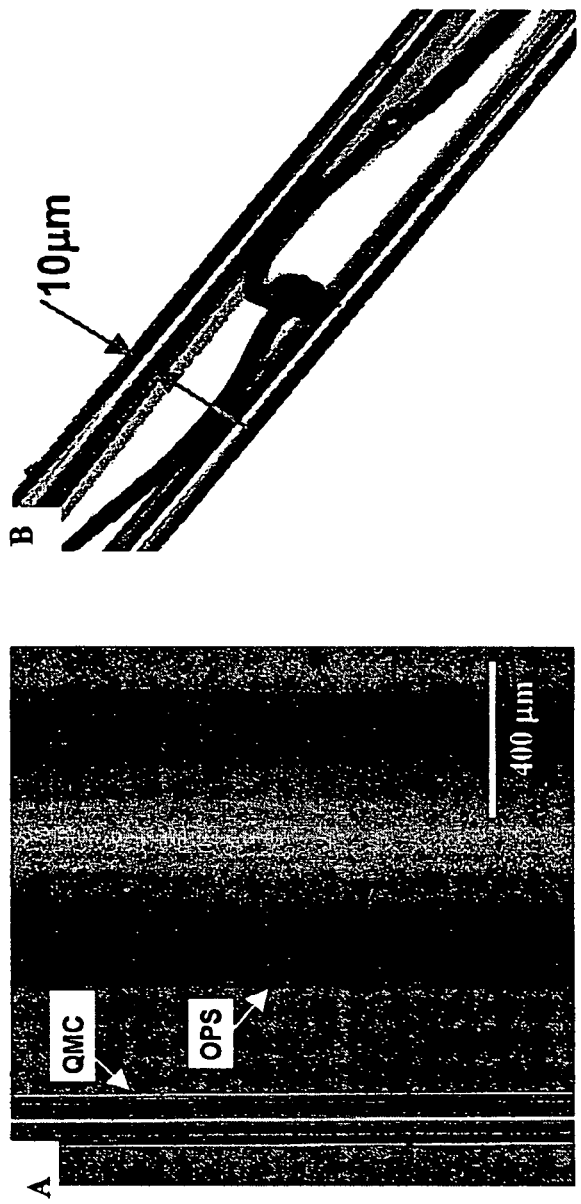
FIGS. 5A and 5B are pictures showing the QMC and the OPS.

A commercially available version of the OPS (MTG-Medical Technological Vertriebs, GMBH) was used. The thermal conductivity of these PVC straws is 0.19 W m$^{-1}$ K$^{-1}$. The inner diameter is 0.800 mm and the thickness of its wall is 0.075 mm. The QMC used (The Charles Supper Company, Inc.) have an inner diameter of 0.180 mm and a wall thickness of 0.010 mm (FIG. 5A). These geometrical improvements (4.44 times smaller in diameter and 7.50 times thinner) translate not only into a faster heat transfer, but also into a ~20 times reduction in volume of the contained solution (for a given height). Additionally, the crystalline structure of the quartz gives it a high anisotropic thermal conductivity: 6.5 W m$^{-1}$ K$^{-1}$ perpendicular to the c-axis and 11.3 W m$^{-1}$ K$^{-1}$ parallel to the c-axis. Therefore the thermal conductivity of the quartz is 34.2 and 59.5 times higher than that of PVC, respectively.

Acquisition System

A T-type thermocouple (Omega Engineering, Inc.), 0.025 mm in diameter, was inserted into the container (OPS or QMC) so that its junction was located roughly 10 mm from its distal end (FIG. 5B). A typical cryopreservation solution used in the slow freezing of oocytes was injected into each container mimicking clinical conditions. The temperature was continuously recorded during quenching and warming by the thermocouple, in conjunction with a data acquisition board (Data Translation, DT9805). This USB controlled board features an internal cold junction as well as an excessively high data acquisition rate (up to 1.2 ksamples/s). For these studies, an acquisition rate of 625 samples/s was used. This rate allowed for an adequate number of points to be taken during quenching, while minimizing the effects of noise from external factors.

A precise protocol was executed for the quenching and warming of each sample: the straws were filled with the chosen solution, kept in the air (temperature around 20° C.) and quenched into nitrogen. A constant dipping rate was maintained for each quench. Once submerged, the sample was held still until the thermocouple's temperature met that of the nitrogen. The sample was then removed and quickly plunged into a water bath at 37° C. The aforementioned data acquisition system was used to obtain thermal histories of the cryopreservation solution during this cycle. This process was repeated ten times for each of the following four cases: OPS in liquid nitrogen, QMC in liquid nitrogen, OPS in slush nitrogen and QMC in slush nitrogen.

Slush Nitrogen Preparation

To make slush nitrogen, a vacuum chamber and pump were used. A Styrofoam container holding 750 ml of liquid nitrogen was placed inside the chamber. The vacuum pressure in the cell was then reduced to 6500 Pa. The nitrogen was left at this pressure for 15 minutes and then removed. As a result, two-phased slush nitrogen was obtained. Liquid nitrogen has a temperature of −196° C. Slush nitrogen has a temperature of roughly −205° C. to −210° C. The main benefit of quenching with the slush over liquid nitrogen however, does not come from this temperature difference, but from a reduction of vaporization when submitted to relatively high temperatures. This reduction of vaporization exposes the sample to a more direct contact with the cryogenic media and in this way increases the cooling rate. To maximize this effect, all measurements were taken within one minute of the slush's removal from the vacuum chamber.

Solution

The solution within the sample containers was the same in the four studied cases. It consisted of 1.5 M 1,2-propanediol and 0.3 M sucrose (Sigma-Aldrich) in 1×PBS (Gibco Life Tech.). This solution, typically not vitrifiable, was chosen because it is of high interest in the slow freezing of human oocytes (Bianchi et al., Hum. Reprod. 20:1078-1083, 2005; Boldt et al., Hum. Reprod. 18:1250-1255, 2003; Borini et al., Hum. Reprod. 21:512-517, 2006; Porcu et al., J. Assist. Reprod. Gen. 16:283-285, 1999) and because of its non-toxic nature. The significantly higher cooling and warming rates achieved through the use of the quartz micro-capillaries opens the possibility of using this convenient solution for cell (e.g., oocyte) vitrification.

Statistics and Data Analysis

As a result of the previously discussed measurements, four sets of data were collected and analyzed, each containing complete thermal histories, cooling rates, and warming rates of ten repetitive preservation cycles. The numerical values reported below were obtained by averaging the data collected from the ten different preservation cycles, all of them expressed as ° C./min (average±SEM, n=10). In the case of determining cooling and warming rates, three temperatures were taken as starting or ending points: 20° C., −20° C., and −150° C. Room temperature (i.e., 20° C.) was chosen as the initial temperature, since this is the temperature at which the sample starts out at on the lab bench; −150° C. was chosen as an end temperature since it is below the eventual glass transition temperature. The other key temperature, −20° C., was chosen because it is below the ice crystallization temperature, therefore, the effect of ice formation is not considered when using it to calculate the cooling or warming rates, thus uncoupling this effect from others and therefore helping to understand the physics behind the measured rates.

Results

CASE 1: OPS in Liquid Nitrogen

Figure 6:
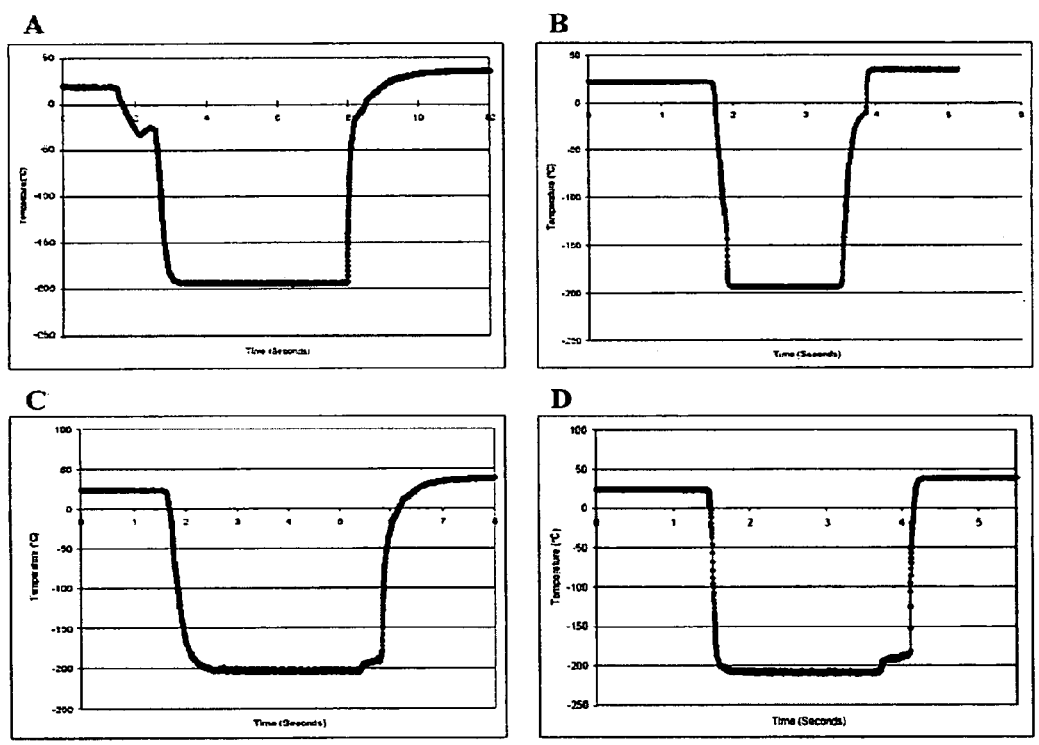
FIGS. 6A-6D are graphs showing the thermal history for the OPS and QMC under various conditions.

FIG. 6A shows the thermal history resulting from plunging the OPS into liquid nitrogen. During the cooling process it is easy to identify the ice formation peak (time ~2.5 s). This peak is generated by the release of latent heat during ice crystallization, indicating clearly that this solution cannot be vitrified when stored in the OPS and plunged into liquid nitrogen. A second indication of the formation of ice crystals can be observed during thawing (FIG. 6A), where the corresponding curve shows a sudden absorption of energy (time ~8.3 s) at the melting point of the solution. It is important to stress the fact that the cooling rates reported depend on the interval of temperatures considered and the kind of solution tested. The cooling rate is very slow (5700±200° C./min), between 20° C. and −150° C., due to the ice formation process. When the crystallization is complete and the solution solidifies, the cooling rate increases significantly between −20° C. and −150° C. (10300±800° C./min). The corresponding effect is also present during warming. The warming rate is 39000±1000° C./min between −150° C. and 20° C. However, when measured between −150° C. and 20° C., this rate decreases to 11300±400° C./min, because the melting process is incorporated in this temperature range.

CASE 2: QMC in Liquid Nitrogen

FIG. 6B depicts the thermal history resulting from the use of the QMC quenched in liquid nitrogen. A significant improvement is seen when comparing this thermal history to that of the OPS in FIG. 6A. In this case, no latent heat release during cooling manifested, which would typically indicate that crystallization did not occur. However, heat absorption during warming is evident and denotes that ice was formed during the preservation cycle. In this case the cooling rate was found to be 30000±3000° C./min between 20° C. and −150° C. The warming rate was 26000±2000° C./min between −150° C. and 20° C. The use of QMC instead of the conventional OPS increases the cooling rate over 6 times, and the warming rate by almost 3 times within the relevant interval of temperature.

CASE 3: OPS in Slush Nitrogen

FIG. 6C depicts the thermal history resulting from the use of the OPS in slush nitrogen. In this case, no latent heat release is reflected in the thermal history during cooling, nor was any melting detected during warming. In principle, this could be an indication of the vitrification of the solution. However, this phenomenon can also be attributed to the fact that the extent of crystallization and melting was too small and/or to fast to be detected. In order to determine whether crystallization actually occurred, one can visually inspect the transparency of the sample after plunging. All of the samples tested appeared white, not transparent, an indication that vitrification was not achieved. Although the OPS quenched in slush nitrogen did not appear to provide vitrification of this solution, a significant improvement in the cooling rates was obtained: 40000±10000° C./min between 20° C. and −150° C. As expected, very little improvement in the warming rates were obtained between −150° C. and 20° C. (17000±300° C./min). This is an indication that the main role of the nitrogen slush is to reduce the nitrogen vapor layer that forms around the sample when quenching, something not present during warming.

In this case, as well as in the next one, it was observed that at the initiation of the warming profile the temperature rose, then stabilized at −196° C., and after a while it rose again (FIGS. 6C and 6D). This stabilization at −196° C. corresponds to the phase transition of the thin layer of nitrogen attached to the external walls of the container, from slush nitrogen to liquid nitrogen, during which the temperature keeps constant.

CASE 4: QMC in Slush Nitrogen

FIG. 6D shows the thermal history of the QMC plunged into slush nitrogen. Like that of the OPS quenched in slush nitrogen, the thermal history shown in this figure reveals no indication of a freezing or melting process. When the sample was inspected directly after quenching, it appeared transparent. This is an indication that vitrification occurred. The results revealed that the combination of slush nitrogen and quartz micro-capillaries raised the cooling rate to 250000±30000° C./min, between 20° C. and −150° C. This cooling rate represents a real qualitative and quantitative improvement over OPS. The use of the QMC with slush nitrogen enables vitrification while reducing the CPA concentration to a non-toxic level, allowing the vitrification approach for important cell types in an effective way. In this case, as in the case of the OPS, no significant improvements in the warming rate can be attributed to the use of slush nitrogen over liquid nitrogen.

Summary of OPS and QMC Results

Figure 7:
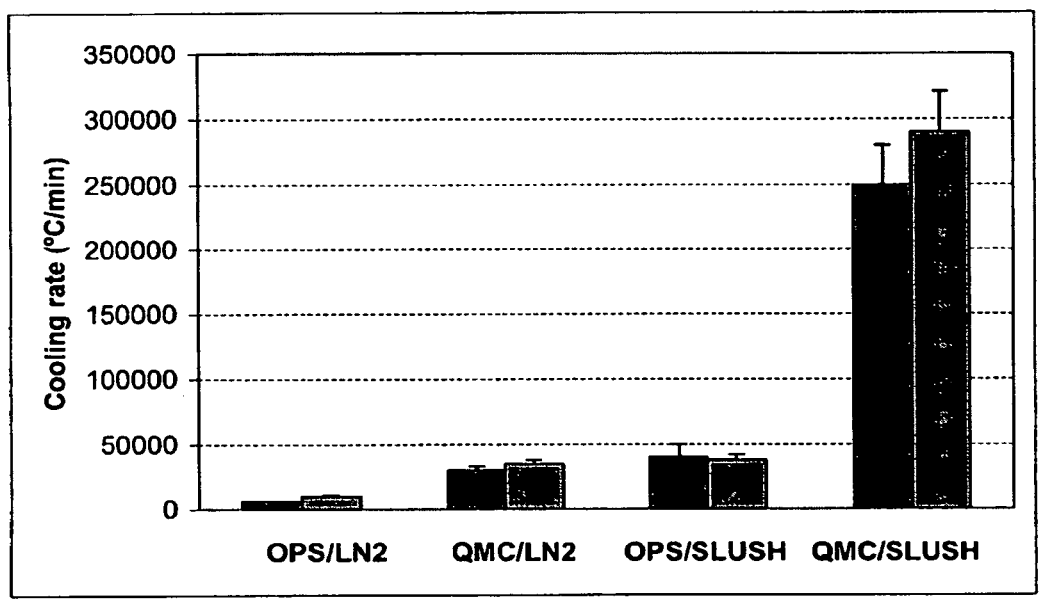
FIG. 7 is a graph showing the cooling rates when quenching OPS and QMC into liquid nitrogen or slush nitrogen. The red bars are cooling rates from 20° C. to −150° C. The blue bars are cooling rates from −20° C. to −150° C. When the technique of OPS in liquid nitrogen is compared with that of QMC in slush nitrogen the difference is evident. The use of QMC in slush nitrogen increases the cooling rate one order of magnitude over other approaches developed to reach high cooling rates for cell vitrification.

FIG. 7 shows a summary of the OPS and QMC cooling rates between 20° C. and −150° C. (red bars) and between −20° C. and −150° C. (blue bars). For both temperature ranges, the QMC in the slush showed significantly faster cooling rates compared to the results of the OPS in liquid nitrogen and slush nitrogen.

Figure 8:
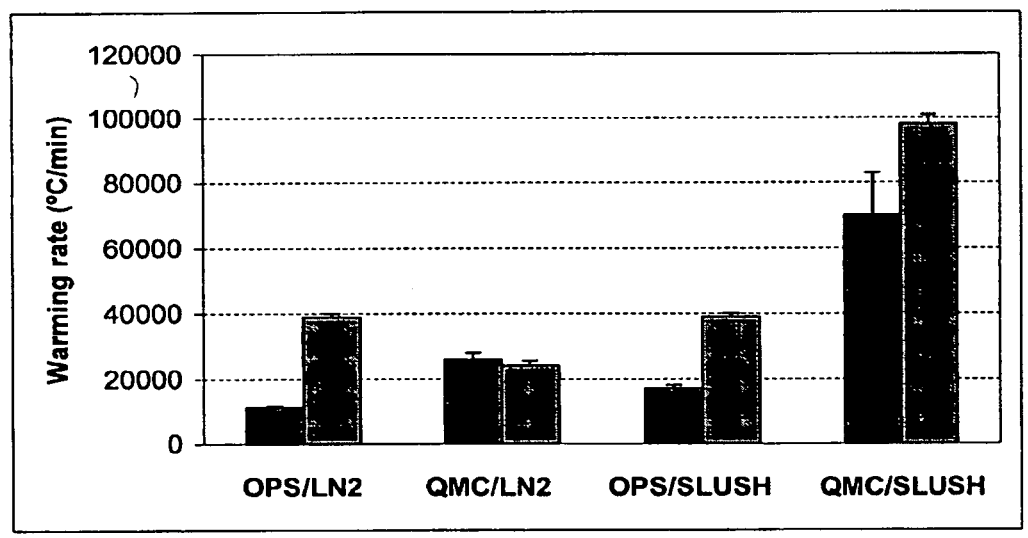
FIG. 8 is a graph of the warming rates for OPS and QMC when warmed in a water bath at 37° C. from liquid or slush nitrogen. The red bars are warming rates from −150° C. to 20° C. The blue bars are warming rates from −150° C. to −20° C. The advantages of warming QMC from slush nitrogen are obvious, taking into account the importance of achieving high warming rates to avoid devitrification or recrystallization. In the case of liquid nitrogen, the warming rate for OPS is higher than for QMC (blue bars) because the extent of ice formation (with high thermal diffusivity) in OPS is much more than in the case of QMC.

FIG. 8 shows a summary of the OPS and QMC warming rates between −150° C. and 20° C. (red bars) and −150° C. and −20° C. (blue bars). Again, for both temperature ranges, the QMC in the slush showed significantly faster warming rates compared to the results of the OPS in liquid and slush nitrogen. Nevertheless, at first glance it may appear as if there exists some paradoxical behavior. When one compares the warming rates of the solution inside the OPS and QMC, previously plunged in liquid nitrogen, a faster warming rate is detected in the case of OPS than that of QMC (FIG. 8, blue bars). The more beneficial properties of QMC for heat transfer could in principle make one think that it should be the contrary. To understand this phenomenon, it is necessary to account for the different physical properties of the solution in these two different containers. In the case of OPS, the solution is crystallized while in the QMC case, it is vitrified. Although in the two cases the chemical composition of the solution is the same, in the case where the solution is crystallized, the thermal diffusivity is higher than in the case where the solution is vitrified. Hence, instead of there being paradoxical, the data provides additional proof of the capability of QMC to vitrify the solution and furthermore, it demonstrates very consistent behavior during cooling and warming, and the physical properties of the solution in each case.

The critical cooling rate to achieve vitrification ($V_{cc}$) is a function of the concentration of cryoprotectant. It has been extensively studied in the case of 1,2-propanediol and other alcohols with relevance in cryobiology, although mainly in the range of cooling rates achievable by differential scanning calorimetry (DSC) techniques. However, it is possible to obtain estimates of the critical cooling rates at other temperatures. The presence of sugars in equimolar concentrations has shown to have no effect on $V_{cc}$ in the case of monosaccharides and little effect in the case of sucrose for the concentration used in these studies (0.3 M)(Kuleshova et al., Cryobiology 38:199-130, 1999). The $V_{cc}$ can be inferred from Boutron's semi-empirical theory of glass forming tendency (Boutron, Cryobiology 23:88-102, 1986); it is given by:

$$V_{cc} = \frac{-K_4(T_0)}{A_1(x_g)},$$

where $$A_1(x) = -\ln(1 - x^{1/3}) + \frac{1}{2}\ln(1 + x^{1/3} + x^{2/3}) + 3^{1/2}\arctan\left(\frac{3^{1/2}x^{1/3}}{2 + x^{1/3}}\right).$$

Figure 9:
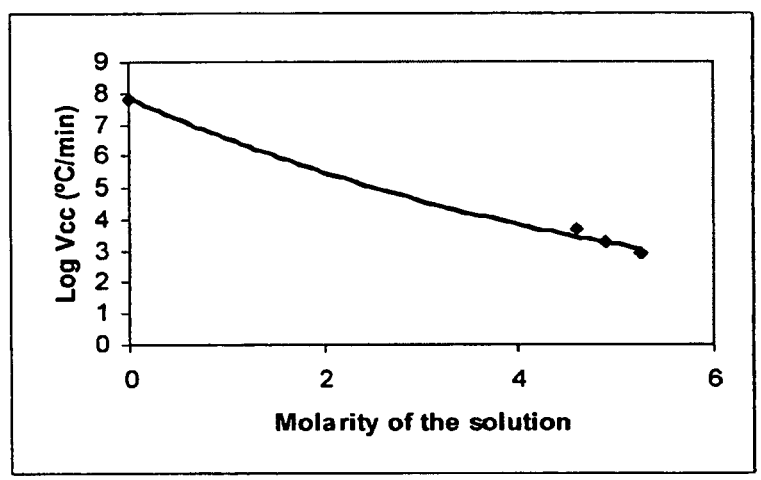
FIG. 9 is a graph of the dependence of the critical cooling rate ($V_{cc}$) with the molarity of the solution for 1,2-propanediol. Points are taken from Johari et al. (Nature 300:552-553, 1987) and Ren et al. (Cryobiology 31:47-56, 1994).

$T_o$ is the initial temperature of crystallization and $x_g$ is the amount of ice formed at the critical cooling rate. Many studies in the literature consider a solution to be vitrified when $x_g \leq 10^{-6}$ (Liu and McGrath, Proc. 2005 IEEE Eng. Med. Biol. 27th Ann. Conference, p. 7501-7504, 2005). $K_4$ is a constant dependent of the solution and can be determined by DSC. Although there is not data for $K_4$ in the available literature for our solution, some estimation can be done. The values of $K_4$ for 40%, 37.5% and 35% (w/w) of aqueous solutions of 1,2 propanediol are 24.1° C./min, 54.1° C./min and 151° C./min (Ren et al., Cryobiology 31:47-56, 1994). These values of $K_4$ give rise to $V_{cc}$ values of $8.0 \times 10^{2°}$ C./min, $1.8 \times 10^{3°}$ C./min and $5.0 \times 10^{3°}$ C./min, respectively. So, a tentative value of $K_4$ for 1.8 M of 1,2-propanediol is $\approx 10^{4°}$ C./min. From the linear relationship between $V_{cc}$ and $K_4$ it is found that $V_{cc}$ should be therefore between $10^5$ and $10^{6°}$ C./min, a value which is in agreement with the cooling rates reported in the above studies. FIG. 9 shows a plot for the information deduced from DSC for 1,2-propanediol as well as for pure water (Johari et al., Nature 300:552-553, 1987), together with an interpolated curve. The exponential fitting of the data is justified by the theory (Ren et al., supra). Again we see that the 1.8 M solution that we used in the present analysis cannot be vitrified at the cooling rates accessible by the use of OPS quenched in liquid nitrogen (5,000 to 20000° C./min). Interestingly, cooling rates of the order of 250000° C./min are necessary, which is in good agreement with the experimental results described.

Example 2

Vitrification of Murine Embryonic Stem Cells

An effective cryopreservation technique was developed using quartz micro-capillaries (QMC) to achieve ultra-fast vitrification using a low, nontoxic level of cryoprotectants (2 M propylene glycol and 0.5 M extracellular trehalose). This technique was investigated by thermal modeling and solution studies. The efficacy of QMC-assisted vitrification on maintaining embryonic stem (ES) cell viability and pluripotency was also investigated. The results indicate that QMC circumvents the physical limitations which previously hindered vitrification at low CPA concentrations. The results also show that QMC-assisted vitrification is an effective technique for preserving sensitive cell types such as murine ES cells.

Materials and Methods
Murine Embryonic Stem (ES) Cell Culture

For the purpose of evaluating the maintenance of embryonic stem cell pluripotency, a green fluorescent protein (GFP)-reporter cell system was used. The R1 murine ES cell line which expresses GFP under control of the Oct4 promoter was kindly provided by Andras Nagy (U. Toronto) (Nagy et al., Proc. Nat. Acad. Sci. USA 90:8424, 1993). The ES cell maintenance media consisted of Knockout DMEM+ 15% Knockout Serum Replacement (Invitrogen, Carlsbad, Calif.) containing 1000 U/ml LIF (Chemicon, Temecula, Calif.). Feeder layer-free ES cells were continually passaged in 0.1% gelatin-coated 75 cm$^2$ flasks in 5% $CO_2$ humidified air at 37° C.

Vitrification Devices

The devices used in these studies include capillary tubes with various dimensions and materials. A micro-drop holding on a copper electro-microscopic grid was also considered in thermal analysis. The configuration of a micro-drop (0.5 µl) on a copper grid is called 'grid' for short in this study. The capillary tubes used include the traditional French type straw (TS, Wipak Medical, Germany) and open pulled straw (OPS, Wipak Medical, Germany), the thin walled quartz micro-capillary (QMC, Wolfgang Muller Glas Technik, Germany), and the thin walled stainless steel micro-capillary (SSMC, Small Parts Inc., Florida, US) as shown in FIG. 1. Also shown in FIG. 1 is the so called superfine open pulled straw (SOPS) which is not significantly different from the open pulled straw visually and in term of vitrification capability (Cuello et al., Theriogenology 62:353, 2004). A summary of the dimensions of the above-mentioned devices is given in Table 2. The thin walled quartz micro-capillary is transparent and has an inner diameter comparable to that of a human oocyte (~120 µm on average), which is much smaller than that of both the traditional French type straw and open pulled straw. The thin-walled stainless steel micro-capillary has a comparable dimension as that of the QMC. The only disadvantage of the SSMC is that it is not transparent for real time monitoring of vitrification.

Thermal Analysis

Figure 2:
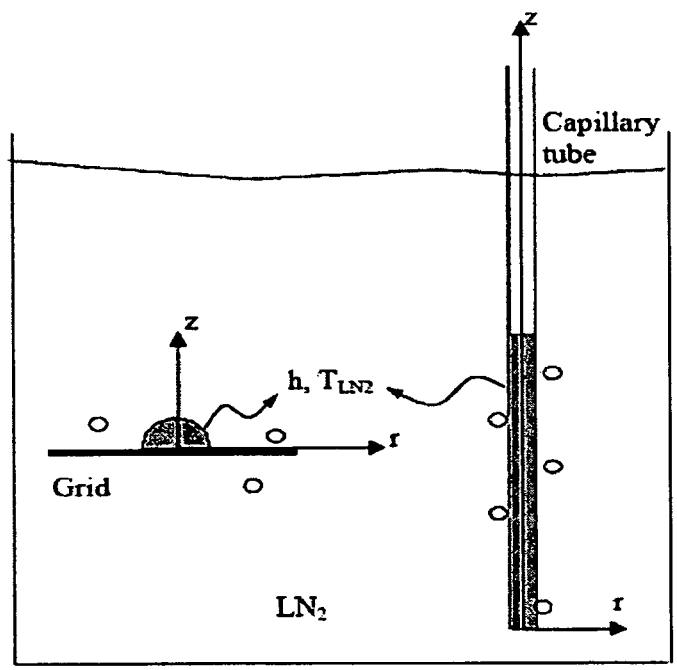
FIG. 2 shows a schema of the physical problem for thermal analysis for both the grid and the capillary design.

A schema of the heat transfer problem involved in these studies is provided in FIG. 2. Due to symmetry of the geometry (i.e., the cylindrical capillary tube and the hemispherical micro-drop) and boundary conditions, a 2D axisymmetric thermal model described by Eq. 17 was used to predict the transient thermal distribution in the cryopreservation solution:

$$\rho_i c_i \frac{\partial T}{\partial t} = \frac{\partial}{\partial z}\left(k_i \frac{\partial T}{\partial z}\right) + \frac{1}{r}\frac{\partial}{\partial r}\left(r k_i \frac{\partial T}{\partial r}\right) \tag{17}$$

where T is temperature, r is radial coordinate, z is axial coordinate, $\rho$ is density, c is specific heat, k is thermal conductivity, and the subscript 'i' represents either the aqueous vitrification solution or capillary wall/grid. No phase change from water to ice was considered in the model since the goal of this study is to vitrify the CPA laden solutions. Convective boundary condition was applied on the external boundaries that have direct contact with the cryogen (i.e., liquid nitrogen):

$$-k_i \frac{\partial T}{\partial n} = h(T - T_{LN2}) \tag{18}$$

where h is the average convective heat transfer coefficient between the external boundaries and liquid nitrogen, n is the outward normal of the external boundary surfaces, and the subscript $LN_2$ represents liquid nitrogen. The boundary condition on all other external surfaces without direct contact with liquid nitrogen was taken as adiabatic. A summary of the thermal properties used is given in Table 1.

With the transient thermal distribution from thermal modeling, the average transient thermal history in the cryopreservation solution was calculated over the whole solution domain using the following equation:

$$T_a = \left( \int_0^{r_s} \int_0^{z_s} 2\pi r T dr dz \right) / V_s \quad (19)$$

where V represents volume and the subscripts a and s represent average and solution, respectively. The average cooling rate from the initial temperature (32° C. here) to −130° C. was calculated by dividing the temperature difference (i.e., 32° C. vs. −130° C.) with the time required to reach −130° C., which was determined from the average transient thermal history in the solution calculated from Eq. 19.

Vitrification of CPA Laden Solutions

Figure 10:
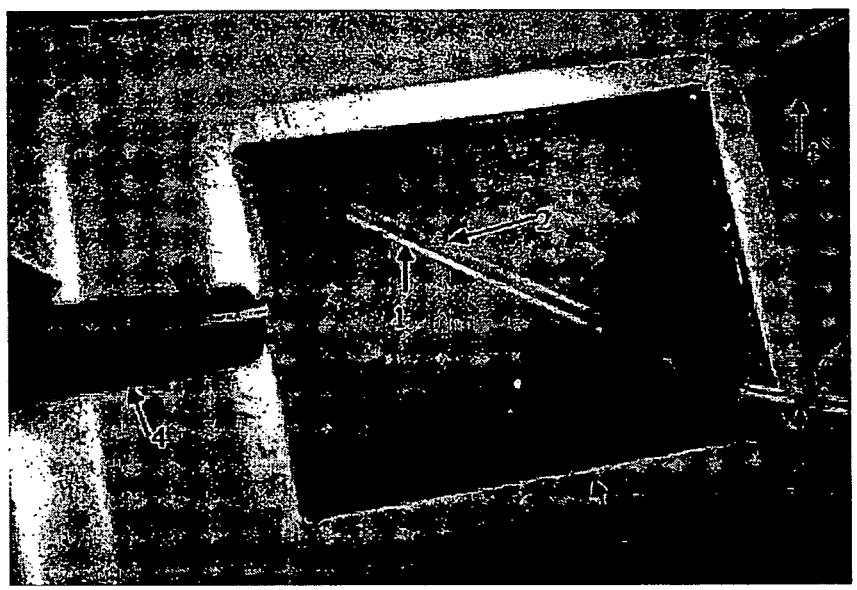
FIG. 10 is a picture of the experimental device used to determine the threshold CPA concentration for complete avoidance of opacity during ultra-fast cooling: 1, a quartz micro-capillary loaded with 7% v 1,2-propanediol in FHM media after rapidly plunging into liquid nitrogen and the whitish appearance inside the tube indicates ice formation or crystallization; 2, a quartz micro-capillary loaded with 14% v 1,2-propanediol in FHM media after rapidly plunging into liquid nitrogen and the clear appearance inside the tube indicates no apparent ice formation or crystallization; 3, A tweezer holding the two quartz micro-capillary together for comparison; 4, two fiber optic lamps to guide focused light onto the quartz micro-capillary to visualize opacity in the quartz micro-capillary; 5, Styrofoam box for holding liquid nitrogen and the inside wall of the box was dyed dark for light contrast to enhance the visibility of opacity.

One convenient way for determining non-vitrification is the appearance of opacity as a result of ice formation when freezing solutions in a straw. If there is no visible opacity, it is called apparent vitrification. Although opacity could be easily identified in the traditional plastic straw using the naked eye, it is very difficult to do so for the quartz micro-capillary due to its small dimension. Therefore, an experimental setup shown in FIG. 10 was designed for visualization of opacity during cooling by directing two focused lights on the capillary held against a dark background for all the devices shown in FIG. 1 except the stainless steel micro-capillary. Shown in FIG. 10 are two quartz micro-capillaries loaded with solutions with two different concentrations of 1,2-propanediol after plunging into liquid nitrogen. The top one containing 2 M 1,2-propanediol (in FHM) is clear while the bottom one containing 1 M 1,2-propanediol (in FHM) is opaque. The solution in the top straw has probably vitrified and the solution in the bottom straw has not. This setup was used to determine the threshold (minimum) CPA concentration required to completely avoid opacity during cooling. Three different CPAs were used including ethylene glycol (EG), 1,2-propanediol (PROH), and their combination in a 1:1 ratio. Various total CPA concentrations from 12% to 30% by volume with 2% increments were studied using both the open pulled straw and the thin walled quartz micro-capillary. Since 0.2-1 M sucrose or trehalose has been used in essentially all studies for cryopreservation of mammalian oocytes by both slow freezing and vitrification, further studies were also performed using the quartz micro-capillary for solutions with 0.5 M sucrose or trehalose plus 1.5 M, 2.0 M, and 2.5 M PROH, respectively. The solutions can be loaded into the open pulled straw and quartz micro-capillaries by capillary action while it can be expelled out of the capillaries by using a micro-syringe attached with a soft PEP polymer needle tip to push from the end of the capillaries with a bigger opening.

Cryopreservation of Embryonic Stem Cells by Vitrification

On the day of experiment, the attached cells were lightly trypsinized for 3-5 minutes and collected. The cells were pelleted at 100×g for 5 minutes and resuspended in cold stem cell media supplemented with 1.5 M 1,2-propanediol (Sigma, St Louis, Mo.) and incubated on ice for 10 minutes. The cells were then spun down at 100×g for 3-5 minutes and resuspended in 1 ml first vitrification solution for 10 minutes. The cells were then spun down at 100×g for 3-5 minutes and resuspended in the second solution at $10 \times 10^6$/ml for another 10 minutes. The first vitrification solution was made of ES cell maintenance medium supplemented with 1.5 M 1,2-propanediol, while the second solution was supplemented with 2 M 1,2-propanediol and 0.5 M trehalose (Ferro Pfanstiehl Laboratories, Inc., Waukegan, Ill.). Cells were also cryopreserved using either 0.5 M trehalose or 2 M 1,2-propanediol only for comparison. When using 0.5 M trehalose alone, the cells were suspended ($10 \times 10^6$/ml) and incubated in ES cell maintenance medium supplemented with 0.5 M trehalose for 10 min at 4° C. and then loaded into the quartz micro-capillary for cooling. In the case of 2 M 1,2-propanediol only, cells were suspended and incubated in 1 ml of the above-mentioned first vitrification solution for 10 minutes, spun down, resuspended ($10 \times 10^6$/ml), and incubated in ES cell maintenance medium supplemented with 2 M 1,2-propanediol. The pH of all solutions was carefully adjusted to 7.2~7.4. The cell suspension was then loaded into a quartz micro-capillary tube. The cell suspension in the quartz micro-capillary was cooled by plunging the micro-capillary into liquid nitrogen and left in liquid nitrogen for 3-5 minutes. The cryopreserved cell suspension was then warmed by plunging the quartz micro-capillary into 1×PBS supplemented with 0.2 M trehalose at room temperature. The cell suspension in the quartz micro-capillary was then expelled into 1 ml warm (37° C.) ES cell medium supplemented with 0.2 M trehalose and incubated for 10-15 minutes. The 1 ml medium with ES cells was then transferred into 9 ml warm stem cell medium and incubated for another 10-15 minutes. The cells were then spun down, resuspended in 1.5 ml medium at room temperature, and cultured in a 35 mm Petri dish coated with 25 μg/ml fibronectin (Chemicon) for further study. Control cells went through the same procedure except cooling and warming.

Cell Attachment and Proliferation Post Vitrification

Cell attachment and growth was determined by counting the number of cells per field under a 10× objective. At least fifteen randomly selected fields of view (10×) were used for each sample. The attachment efficiency was calculated as the ratio of the total number of cells per field of a cryopreserved sample to that of the control non-frozen sample at day 1. To assess the proliferation of the attached cells, the total number of cells per field was further monitored for 4 days.

Pluripotent Properties of ES Cells Post-Vitrification

To determine whether the embryonic stem cells retained their pluripotent properties post-cryopreservation, three different types of assays that are characteristic to murine embryonic stem cells were performed: the expression of transcription factor Oct-4, the expression of membrane surface glycoprotein SSEA-1, and the elevated expression of the enzyme alkaline phosphatase. For immunofluorescence staining of SSEA-1, fixed ES cells were permeabilized with 0.4% Triton X-100 and blocked against non-specific binding with 2% BSA. The monoclonal antibody against SSEA-1 (clone MC-480) was purchased from Chemicon. Antibody localization of SSEA-1 was performed using a Texas Red conjugated goat anti-mouse F(ab')$_2$ fragment antibody (Rockland, Gilbertsville, Pa.). Alkaline phosphatase staining was observed by incubating naphthol AS-BI phosphate and fast red violet solutions (Chemicon) with 4% paraformaldehyde-fixed ES cells for 15 minutes.

Results

Effects of Capillary Dimensions on Cooling Rate

Figure 11:
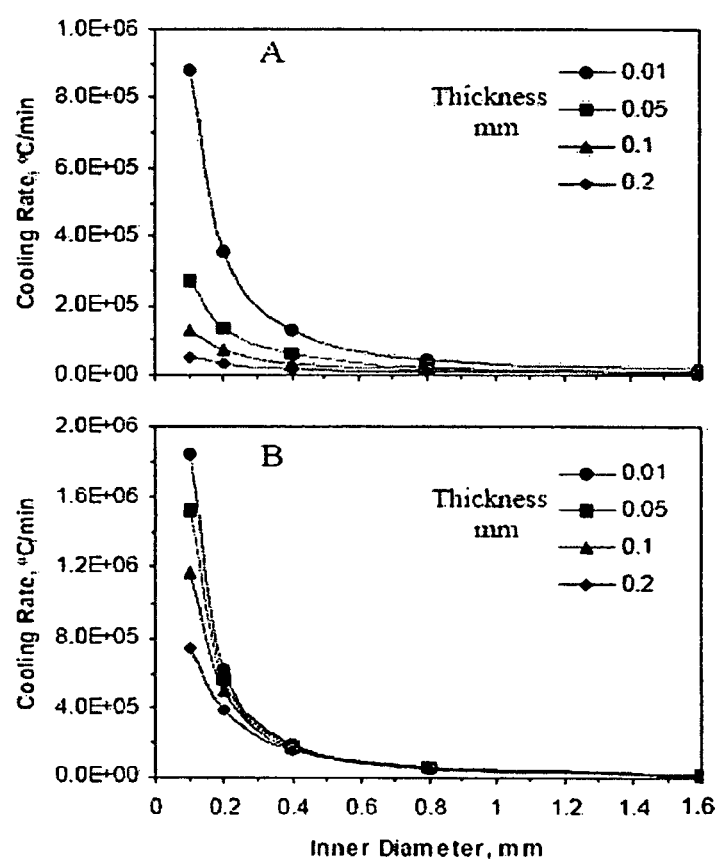
FIGS. 11A and 11B are graphs showing the predicted average cooling rate for both plastic (FIG. 11A) and quartz (FIG. 11B) capillaries with varying inner diameter and wall thickness. The boiling heat transfer coefficient was assumed to be $5\times10^4$ W m$^{-2}$ K$^{-1}$ for the predictions.

The effect on cooling rate of capillary dimensions including the inner diameter (ID) and wall thickness (WT), is shown in FIGS. 11A and 11B for two different wall materials: plastics and quartz, respectively. It is clear from FIG. 11 that the cooling rate increases in a very strong nonlinear fashion with the decrease of the inner diameter for both wall materials, especially when the inner diameter is less than 0.4 mm. The cooling rate also increases significantly with the decrease of wall thickness and this effect is more apparent when the inner diameter is less than 0.4 mm for both materials. These results indicate the importance of micro-machined small and thin capillaries for achieving high cooling rate by plunging the capillaries into liquid nitrogen.

Effects of Capillary Wall Material on Cooling Rate

Figure 12:
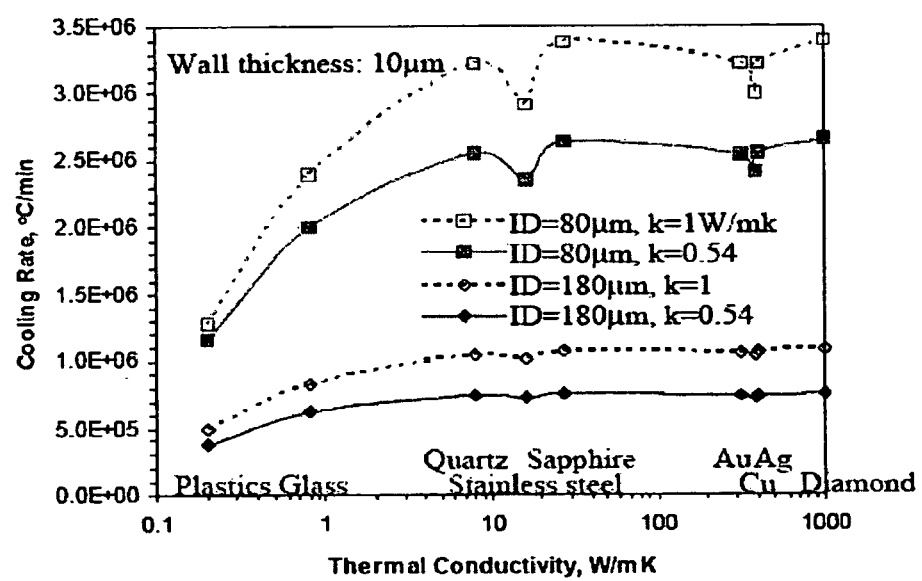
FIG. 12 is a graph of the predicted cooling rate vs. thermal conductivity of various wall materials for capillaries with 10 μm wall thickness and two different inner diameters: 80 μm and 180 μm. The boiling heat transfer coefficient was assumed to be $5\times10^4$ W m$^{-2}$ K$^{-1}$ for the predictions.

FIG. 12 shows the effect of capillary wall material on cooling rate for two different capillary dimensions: ID=~180 μm and 80 μm with 10 μm wall thickness. It is clear that the cooling rate increases when using more conductive material from plastics to quartz.

Comparison of Average Cooling Rate for Available Devices

Figure 13:
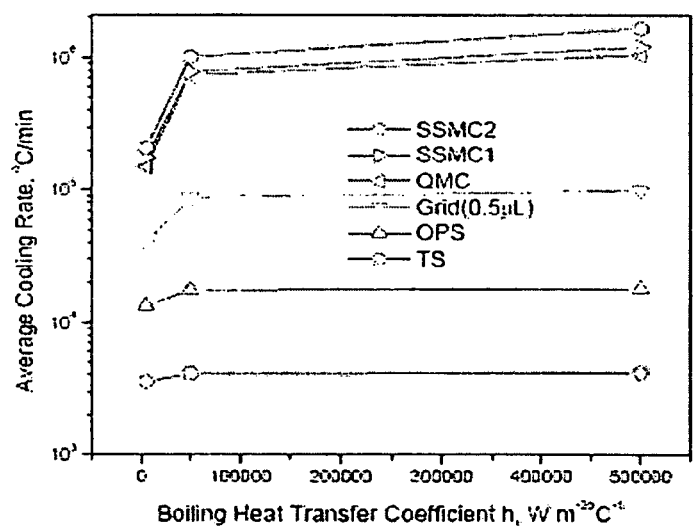
FIG. 13 is a comparison of the predicted cooling rate for the reported and proposed devices for vitrification of mammalian cells: the devices were listed with dimensions in Table 2.

FIG. 13 shows a comparison of the cooling rate for the available devices given in Table 2 as a function of the boiling heat transfer coefficient between the capillary wall and adjacent liquid nitrogen. The cooling rate is almost the same for the two stainless steel and quartz micro-capillaries, which is about one order of magnitude greater than that of the grid design, two orders of magnitude greater than that of the open pulled straw, and three orders of magnitude greater than that of the traditional straw. It is worth noting that the boiling heat transfer coefficient does have a significant effect on cooling rate when it is lower than $10^5$ W/(m$^{2\circ}$ C.), especially for the quartz and stainless steel micro-capillaries. Therefore, it is important to plunge the capillary very fast in the freezing medium (liquid nitrogen) during freezing to create a forced convective boiling flow and enhance the heat transfer coefficient on the boundary.

Vitrification of the Solution of Various Cryoprotectants

The threshold concentration for the complete absence of opacity of three different cryoprotectants, ethylene glycol, 1,2-propanediol, and their combination in a 1:1 ratio, was determined for both open pulled straw and quartz micro-capillary. A typical experimental matrix is given in Table 3.

TABLE 3

Experimental matrix.

| CPA Volume (% v) | | 12 | 14 | 16 | 18 | 20 | 22 | 24 | 26 | 28 |
|---|---|---|---|---|---|---|---|---|---|---|
| Ethylene glycol | OPS | N/D | N/D | N/D | N/D | – | –/+ | + | + | + |
| (EG) | QMC | – | ––/+ | –/+ | –/+ | + | N/D | N/D | N/D | N/D |
| 1,2- | OPS | N/D | N/D | – | ––/+ | –/+ | + | + | + | N/D |
| Propanediol (PROH) | QMC | –/+ | + | + | N/D | N/D | N/D | N/D | N/D | N/D |
| EG:PROH | OPS | N/D | N/D | – | –––/+ | –/+ | + | + | + | N/D |
| (1:1) | QMC | –/+ | –/+ | + | + | N/D | N/D | N/D | N/D | N/D |

OPS: Open pulled straw;
QMC: 0.2 mm OD Quartz micro-capillary

Figure 14:
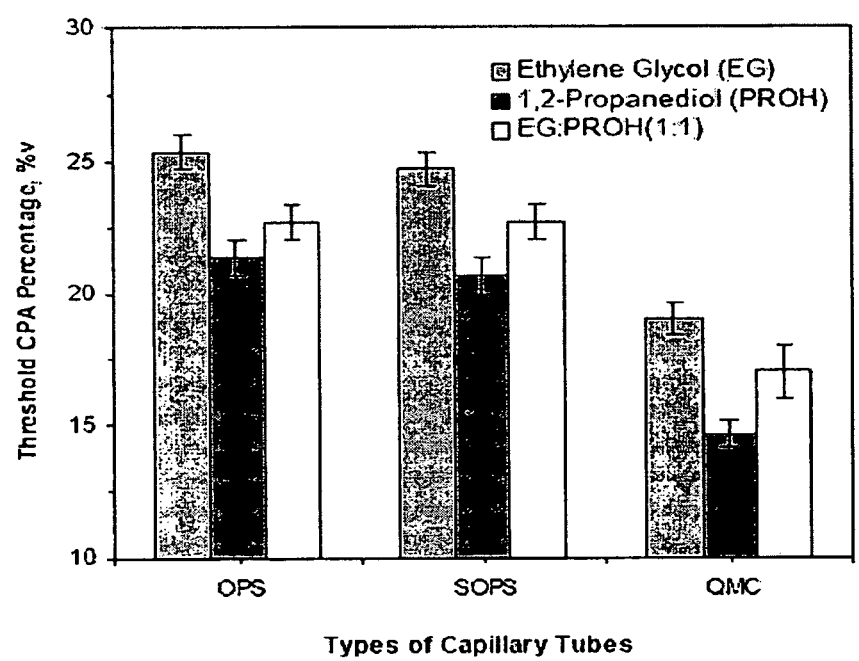
FIG. 14 is a graph of the threshold concentration for the complete absence of opacity when cooling various CPA solutions in the open pulled straw (OPS), superfine open pulled straw (SOPS), and the quartz micro-capillary (QMC).

The average results of three separate runs with solutions made in three different days are given in FIG. 14. Also shown in this figure are the results for the so-called superfine open pulled straw (SOPS), which is not different from those of the open pulled straw, and is in agreement with the results reported by Cuello et. al. (Theriogenology 62:353, 2004) using the same two devices for the vitrification of porcine embryos. For both open pulled straw and quartz micro-capillary, FIG. 14 shows that the threshold concentrations required for 1,2-propanediol (PROH) is ~5% v and 2.5% v lower than those of ethylene glycol (EG) and the combination of EG and PROH in a 1:1 ratio, respectively. The 5% v difference between ethylene glycol and 1,2-propanediol is significant since it means that the difference is ~1 M in terms of molar concentration. Most importantly, FIG. 14 also shows that the threshold concentrations required for the quartz micro-capillary is 5-7% v lower than those required for the open pulled straw for all the three different combinations of cryoprotectants, which again is significant since it represents ~1 M difference in terms of molar concentration. Putting all these together, the threshold concentration for the complete absence of opacity is only ~2 M when adopting micro-capillary and 1,2-propanediol, while it is ~4 M when using open pulled straw and ethylene glycol. Further experiments were also performed on FHM and ES cell medium with 0.5 M trehalose plus 1.5 M (~1% v), 2 M (~15% v), and 2.5 M (19% v) 1,2-propanediol. No opacity was observed after plunging these solutions contained in the quartz micro-capillary in liquid nitrogen.

Attachment Efficiency of ES Cells Post Vitrification

Figure 15:
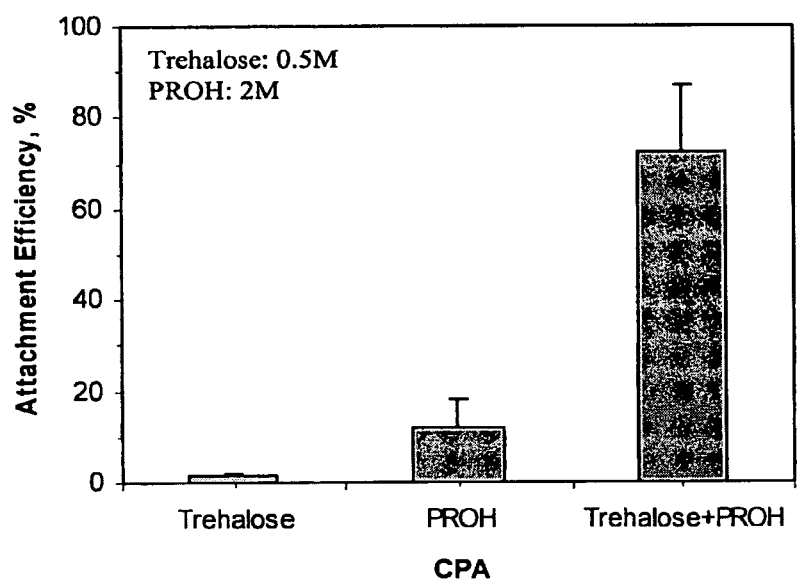
FIG. 15 is a comparison of the attachment efficiency (normalized to control) of mouse embryonic stem (ES) cells cryopreserved using three different cryoprotectants and concentrations in the quartz microcapillary. The concentrations of trehalose and 1,2-propanediol (PROH) are 0.5 M and 2 M for all the conditions, respectively. Each data point represents the average of at least three different runs at three different days and the error bar represents the standard deviation.

FIG. 15 shows the attachment efficiency of ES cells post-freezing using 0.5 M trehalose, 2 M 1,2-propanediol (PROH), and the combination of 0.5 M trehalose and 2 M PROH. Only a minimum amount of cells can attach when using either 0.5 M trehalose or 2 M PROH alone. The attachment efficiency, however, is high (72%) when using the combination of 0.5 M trehalose and 2 M PROH. Therefore, trehalose and PROH have a synergistic effect on protecting ES cells from damage during cryopreservation.

Proliferation of ES Cells Post Vitrification

Figure 16:
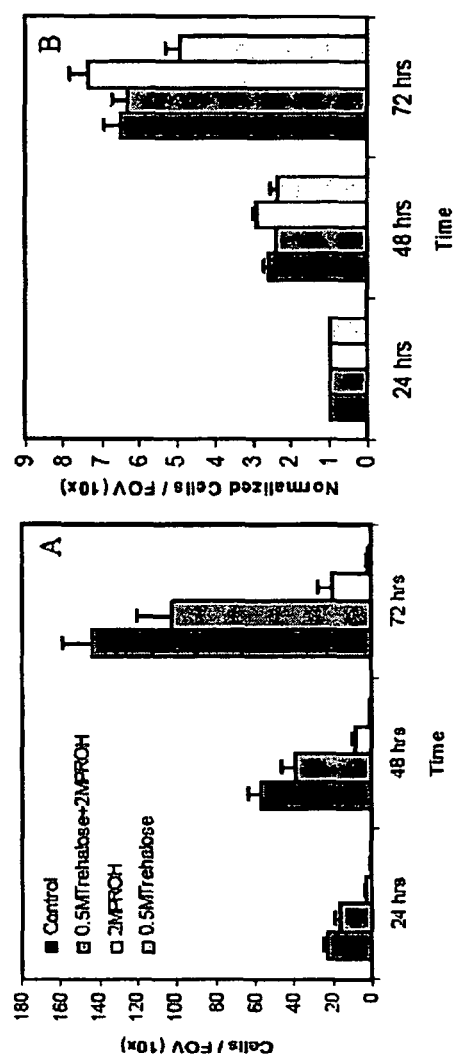
FIGS. 16A and 16B are graphs showing the absolute (FIG. 16A) and normalized (FIG. 16B) number of cells per field of view under a 10× objective for both control (non-frozen) and cryopreserved mouse embryonic stem cells. Each data point represents the average of at least three different runs at three different days and the error bar represents the standard deviation.

FIG. 16A shows the proliferation of attached ES cells post-vitrification. The number of cells per field for both the cryopreserved samples and control non-frozen samples increased in a very similar fashion. The similarity in growth patterns is more evident in FIG. 16B, which shows the normalized number of cells per field of view calculated as the ratio of the cells per field of view at days 2-3 with respect to that of day 1. The population doubling time for all cell groups was approximately 21 hours. Therefore, murine embryonic stem cells post-vitrification preservation can grow normally after attachment.

Pluripotent Properties of ES Cells Post Vitrification

Figure 17:
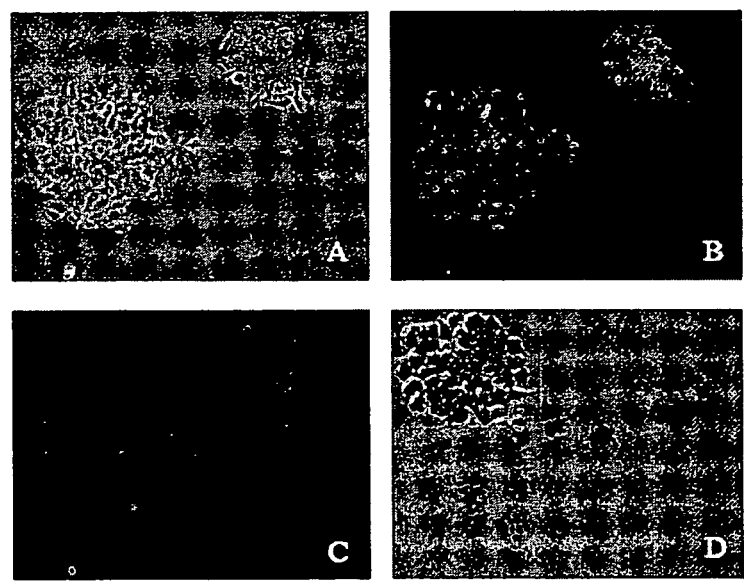
FIGS. 17A-17D are a series of photomicrographs showing the morphological characteristics of the ES cells post vitrification.

As shown in FIGS. 17A-17D, ES cells post-vitrification retained the morphological characteristic of undifferentiated stem cells to form cell colonies (FIG. 17A). Pluripotency of the ES cells was verified by the expression of the green fluorescent protein OCT-4 (FIG. 17B) and the membrane surface glycoprotein SSEA-1 (FIG. 17C), and the elevated expression of intracellular alkaline phosphatase (FIG. 17D). The positive staining of the three different markers that are characteristic to murine embryonic stem cells suggests that the murine ES cells retained their pluripotent properties post-vitrification preservation. These results indicate that vitrification by ultra-fast cooling using a very low concentration of cryoprotectant (2 M 1,2-propanediol) is a viable and effective approach for cryopreservation of murine ES cells.

Example 3

Vitrification of Hepatocytes

The vitrification technique was also tested using primary liver cells (hepatocytes) due to their sensitivity to stress, and importance in liver tissue engineering and availability.

Figure 18:
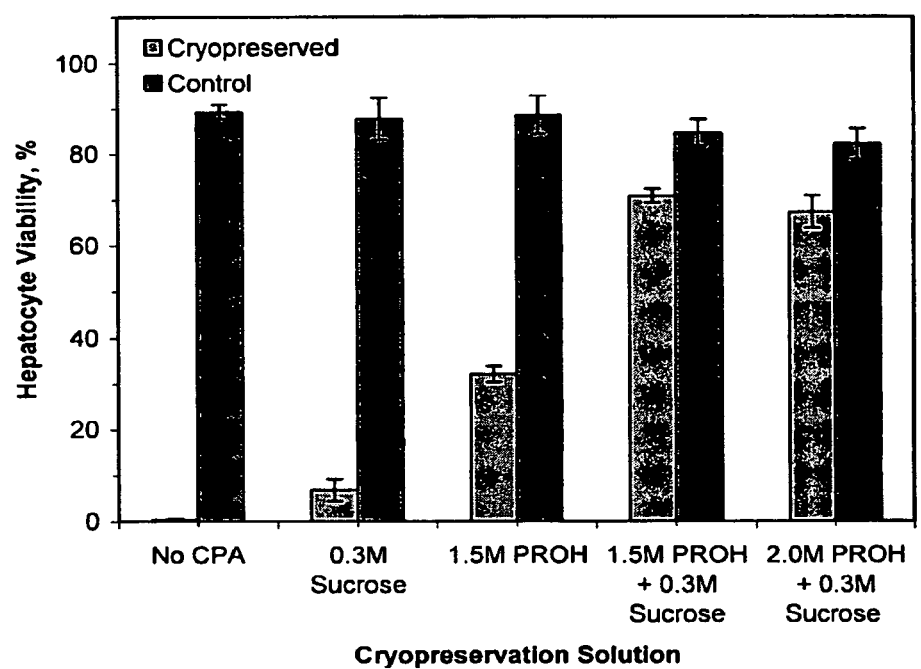
FIG. 18 is a graph depicting the percentage of viable primary rat hepatocytes in control and vitrification samples containing no cryoprotective agent (no CPA); 0.3 M sucrose; 1.5 M 1,2-propanediol (PROH); 1.5 M PROH+0.3 M sucrose; or 2.0 M PROH+0.3 M sucrose. The viability assay is the exclusion of trypan blue.

The cell viability of hepatocytes was determined immediately post-cryopreservation in quartz micro-capillaries (QMC) in the presence of either no CPA; 0.3 M sucrose; 1.5 M 1,2-propanediol (PROH); 1.5 M PROH and 0.3 M sucrose; or 2.0 M PROH and 0.3 mM sucrose. The number of viable cells was determined in both vitrified samples as well as non-vitrified controls (i.e., no freezing). Cell viability was quantified by the exclusion of trypan blue. Not surprisingly, cells cryopreserved in the absence of CPA were essentially all dead (FIG. 18). There was only ~35% survival for cells loaded with 1.5 M PROH prior to cryopreservation. Sucrose (0.3 M) was then added to the cryopreservation solution with 1.5-2 M PROH. Sucrose does not enter into cells as it is impermeable to the plasma membrane. When 0.3 M sucrose was added to the cryopreservation solution, the immediate viability jumped to ~75%. Use of 0.3 M sucrose alone for cryopreservation resulted in less than 10% cell survival. Therefore, vitrification utilizing both 0.3 M sucrose and 1.5-2 M PROH resulted in a greatly enhanced cell survival following cryopreservation.

Figure 19:
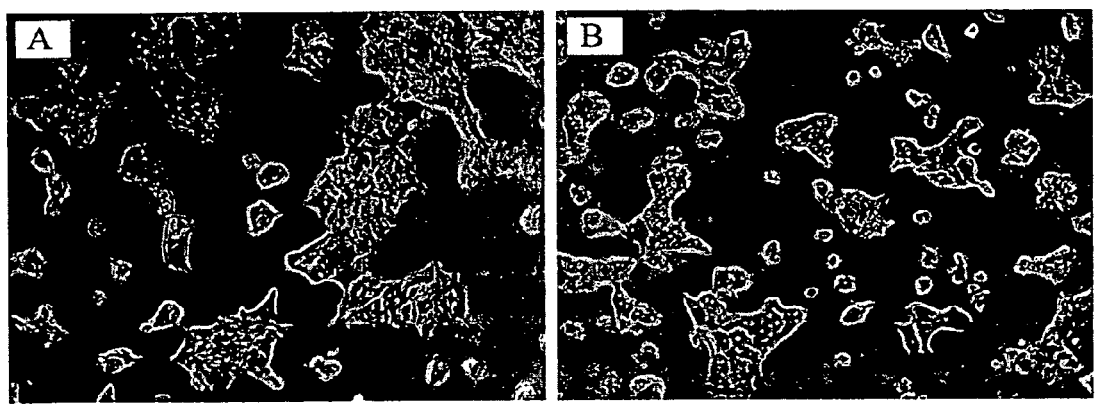
FIGS. 19A and 19B are photomicrographs (10×) depicting typical phase contrast image of both control (FIG. 19A) and vitrified (FIG. 19B) primary rat hepatocytes cultured for 3 days in a double collagen culture system.

The morphology of both control and vitrification cryopreserved hepatocytes (2 M PROH and 0.3M sucrose in QMC) was also examined (FIGS. 19A-19B). The warmed hepatocytes were cultured in a double collagen system for 3 days before observation. As with the control cells, the vitrified hepatocytes retained their phenotypic multi-nuclei polygonal morphology.

Example 4

Vitrification of Fertilized Mouse Oocytes and Human Oocytes

Figure 20:
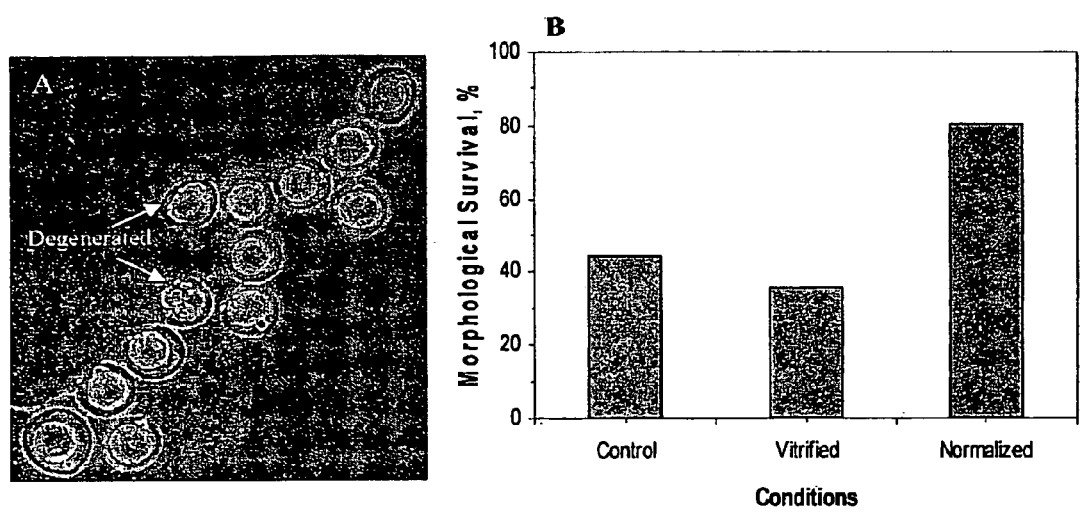
FIGS. 20A and 20B are a photomicrograph and a graph showing the morphological characteristics of fertilized mouse oocytes (zygotes) which are viable (intact zona pellucida and plasma membrane and refractive cytoplasm) and those which are non-viable (Degenerated) (FIG. 20A) and the percentage of fertilized mouse oocytes (zygotes) which have morphological survival characteristics following no treatment or vitrification (FIG. 20B). Following correction for background cell death in the untreated zygotes, over 80% of the zygotes survived the vitrification process. For failed fertilized human oocytes, 8 of 13 retained morphological survival after vitrification using 1.5 M 1,2-propanediol and 0.3 M sucrose.

The morphological survival of fertilized mouse oocytes (zygotes) using 1.5 M PROH and 0.3 M sucrose, and a QMC were examined. The viability of the fertilized mouse oocytes (zygotes) was determined via examination of morphological characteristics (i.e., degenerated cells are deemed non-viable, while cells having intact zona pellucida and plasma membrane and refractive cytoplasm are deemed viable) (FIG. 20A). The cell survival data is normalized to the data for cells which were not vitrified (i.e., not frozen). The normalized percentage of morphological survival of fertilized oocytes (zygotes) is ~80% (FIG. 20B).

Failed fertilized human oocytes were also vitrified using 1.5 M PROH and 0.3 M sucrose, and a QMC as described above. In these studies, 8 out of 13 (~62%) displayed morphological survival.

Example 5

Vitrification of Mammalian Zygotes

A series of experiments were performed to test the tolerance of 2PN stage murine zygotes (Conception Technologies, San Diego, Calif.) to cryopreservation solution exposure, loading/unloading zygotes from quartz micro-capillaries, and ultimately cooling/warming.

Tolerance to Cryopreservation Solution: Comparison Between Two CPA Unloading Protocols The cryoprotective agents used in this study included 1,2-propanediol (PROH, permeable to the plasma membrane of mammalian cells) and the disaccharide trehalose (impermeable to the plasma membrane of mammalian cells). Zygotes were exposed to 2.0 M PROH+0.5 M trehalose solution, then exposed to two different post-warm CPA unloading protocols: (1) with 1.0 M PROH in CPA unloading step 1; and (2) without PROH in CPA unloading step 1. Cleavage rates were 59% for the group exposed to additional PROH (protocol "A") and 87% for the group that was not exposed to the additional PROH during unloading (protocol "B"). The only difference between the protocol "A" group and protocol "B" group was that the former had an additional 5 minutes of exposure to 1.0 M PROH compared to the latter. That additional time of exposure was enough to lower the cleavage, blast, and hatch rates compared to the protocol "B" group. These data suggest there is a harmful effect directly related to time of exposure to PROH particularly during CPA unloading.

Tolerance to Quartz Micro-Capillary Loading and Unloading

Zygotes were exposed to the cryopreservation solution described in section (α) above, then loaded into 200 μm (outer diameter) quartz micro-capillaries. They were subsequently unloaded from the quartz micro-capillaries by injecting a small amount (2-3 droplets) of warm media through the top of the capillaries. Recovery from quartz micro-capillaries was 100% (n=185) across the board. A single zygote was lost through the 4-step CPA unloading process in the protocol "1" group. Cleavage rates were ≥97% across the board. Blast rates were ≥93% for the protocol "2" and sham control groups; blast rates were significantly lower (69%) for the protocol "A" group. These data suggest there was no additional cellular damage related to the quartz micro-capillary system itself.

Cryopreservation Survival

Zygotes were exposed to the cryopreservation solution described above, and then loaded into 200 μm (O.D.) quartz micro-capillaries and plunged into slush nitrogen. Zygotes were warmed by plunging directly into a warm bath composed of 1×PBS and 0.5 M trehalose. As before, zygotes were exposed to two different post-warm CPA unloading protocols: (1) with 1.0 M PrOH in CPA unloading step 1; and (2) without any additional PrOH in CPA unloading step 1. Zygotes were cultured for 2 hours after the initial warming to allow for recovery of normal physiological function.

Results

Figure 21:
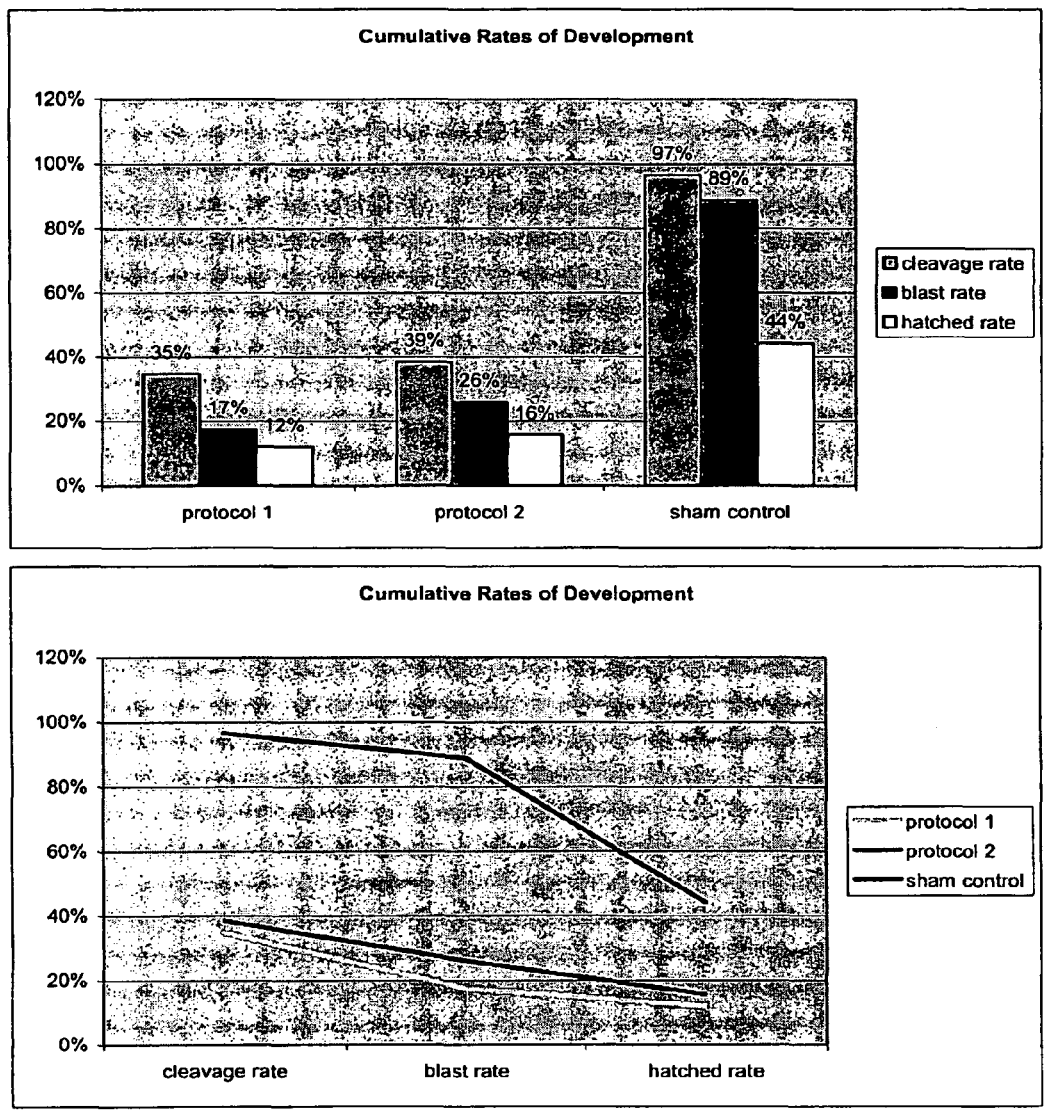
FIG. 21 shows two graphs comparing the percentage of cleavage, blastocyst, and hatching of 2PN stage murine zygotes using two different vitrification protocols with those of sham control. The sham control protocol has the same procedures as those of protocol 2 except cooling and warming.

Post-cryopreservation recovery from the quartz micro-capillaries was ≥93% (n=300) across the board. Of the 283 zygotes recovered, 277 ultimately survived through culture. This represents just a 2% loss of cells during the 4- or 5-step CPA unloading process. Rates of cleavage and blastocyst formation were within the expected range for the sham control (no cool/warm) group: 97% and 89%, respectively (FIG. 21). Both cleavage and blastocyst formation rates were significantly lower for the two cryopreservation groups, though still acceptably high for our purposes (FIG. 21).

The studies show that 2PN stage murine zygotes could survive well post loading and unloading of this amount of cryoprotectants. The studies also show that zygotes could survive well the loading/unloading in and out of the quartz micro-capillary.

Other Embodiments

From the foregoing description, it will be apparent that variations and modifications may be made to the invention described herein to adopt it to various usages and conditions. Such embodiments are also within the scope of the following claims.

All publications, patent applications, and patents mentioned in this specification, including U.S. Provisional Application Ser. Nos. 60/792,019, filed on Apr. 14, 2006, 60/792,020, filed on Apr. 14, 2006, and 60/854,880, filed on Oct. 27, 2006, are herein incorporated by reference to the same extent as if each independent publication, patent application, or patent was specifically and individually indicated to be incorporated by reference.

From the foregoing description, one skilled in the art can easily ascertain the essential characteristics of this invention; can make various changes and modifications of the invention to adapt it to various usages and conditions. Thus, other embodiments are also within the claims.

What is claimed is:

1. A method for cryopreserving a mammalian cell, the method comprising:
    (a) suspending said cell in a vitrification solution comprising one or more cryoprotective agents, wherein a concentration of the combination of all cryoprotective agents in said vitrification solution is less than or equal to 4 M;
    (b) placing said cell in said vitrification solution in a microcapillary tube, wherein said microcapillary tube has a wall made of a material having a thermal conductivity of at least 0.2 W m$^{-1}$K$^{-1}$; and
    (c) cooling said cell in said vitrification solution in said microcapillary tube to a temperature less than or equal to a glass transition temperature of said vitrification solution at a rate greater than 200,000° C./min, wherein said cooling causes vitrification of said cell.

2. The method of claim 1, wherein said cell is an oocyte, a stem cell, an embryo, or a zygote.

3. The method of claim 2, wherein said cell is an oocyte, an embryo, or a zygote.

4. The method of claim 2, wherein said cell is a stem cell.

5. The method of claim 1, wherein said microcapillary tube comprises a wall having a thickness of 10 to 20 μm.

6. The method of claim 1, wherein said microcapillary tube comprises an inner diameter of about 80 to 180 μm.

7. The method of claim 1, wherein said microcapillary tube has a wall made of a material having a thermal conductivity of at least 5 W m$^{-1}$ K$^{-1}$.

8. The method of claim 1, wherein said microcapillary tube has a wall made of a material selected from the group consisting of plastic, glass, quartz, stainless steel, sapphire, silver, copper, diamond, gold, titanium, palladium, and platinum.

9. The method of claim 8, wherein said material is quartz.

10. The method of claim 1, wherein said cell in said vitrification solution is cooled at a rate equal to or greater than 350,000° C./min.

11. The method of claim 10, wherein said cell in said vitrification solution is cooled at a rate equal to or greater than 1,000,000° C./min.

12. The method of claim 1, wherein said at least one cryoprotective agent is selected from the group consisting of a sugar, glycerol, ethylene glycol, 1,2-propanediol, and DMSO.

13. The method of claim 1, wherein said concentration of the combination of all cryoprotective agents in said vitrification solution less than or equal to 3 M.

14. The method of claim 13, wherein said concentration of the combination of all cryoprotective agents in the vitrification solution is less than or equal to 2 M.

15. The method of claim 13, wherein said concentration of the combination of all cryoprotective agents in said vitrification solution is less than or equal to 1 M.

16. The method of claim 13, wherein said concentration of the combination of all cryoprotective agents in said vitrification solution is less than or equal to 0.5 M.

17. The method of claim 13, wherein said concentration of the combination of all cryoprotective agents in said vitrification solution is less than or equal to 0.3 M.

18. The method of claim 1, wherein said vitrification solution comprises at least one nanoparticle or microparticle.

19. The method of claim 18, wherein said nanoparticle or microparticle comprises carbon or a noble metal.

20. The method of claim 18, wherein said nanoparticle or microparticle is selected from the group consisting of gold, silver, titanium, palladium, platinum, and copper.

21. The method of claim 1, wherein said vitrification solution comprises one or more polymers or peptides, or both, that inhibit ice nucleation in said vitrification solution.

22. The method of claim 21, wherein said polymer or peptide is selected from the group consisting of polyvinyl alcohol, polyglycerol, and antifreeze proteins.

23. The method of claim 1, wherein said cell in said vitrification solution is emulsified into a droplet of vitrification solution surrounded by an immiscible biocompatible fluid.

24. The method of claim 23, wherein said immiscible biocompatible fluid comprises an oil.

25. The method of claim 1, further comprising shaking the tube at a frequency of at least 1.0-100 Hz after step (b).

26. The method of claim 1, wherein a wall of said microcapillary tube has a ratio of wall material thermal conductivity (watts per meter kelvin) to wall thickness (meters) of at least 1,000 watts per meter squared Kelvin (Wm$^{-2}$K$^{-1}$).

27. The method of claim 26, wherein said microcapillary tube has a ratio of wall material thermal conductivity to wall thickness of at least 500,000 Wm$^{-2}$K$^{-1}$.

28. The method of claim 26, wherein said microcapillary tube has a ratio of wall material thermal conductivity to wall thickness of at least 5,000 Wm$^{-2}$K$^{-1}$.

29. The method of claim 26, wherein said microcapillary tube has a ratio of wall material thermal conductivity to wall thickness of at least 10,000 Wm$^{-2}$K$^{-1}$.

30. The method of claim 26, wherein said microcapillary tube has a ratio of wall material thermal conductivity to wall thickness of at least 100,000 Wm$^{-2}$K$^{-1}$.

31. The method of claim 1, wherein said cell is cooled by plunging at least a portion of the microcapillary tube from room temperature into slush nitrogen.

32. The method of claim 1, wherein said concentration of the combination of all cryoprotective agents in said vitrification solution is less than or equal to 2 M.

33. The method of claim 1, wherein the one or more cryoprotective agents comprise 1,2-propanediol (PROH) or propylene glycol at a concentration of 1 M to 2 M and a sugar at a concentration of 0.2 M to 1 M.

34. The method of claim 33, wherein the sugar comprises one or more of sucrose, trehalose, raffinose, stachyose, and dextran.

35. The method of claim 34, wherein the cryoprotective agents comprise 1.5 M to 2.0 M PROH and 0.3 M to 0.5 M trehalose.

\* \* \* \* \*

UNITED STATES PATENT AND TRADEMARK OFFICE
CERTIFICATE OF CORRECTION

PATENT NO. : 9,538,745 B2  
APPLICATION NO. : 12/226300  
DATED : January 10, 2017  
INVENTOR(S) : Xiaoming He et al.

Page 1 of 1

It is certified that error appears in the above-identified patent and that said Letters Patent is hereby corrected as shown below:

In the Claims

In Column 32, Line 3, Claim 13, after "solution" insert -- is --.

Signed and Sealed this  
Fourth Day of July, 2017

Joseph Matal  
*Performing the Functions and Duties of the*  
*Under Secretary of Commerce for Intellectual Property and*  
*Director of the United States Patent and Trademark Office*